US008670582B2

(12) United States Patent
Lunner et al.

(10) Patent No.: US 8,670,582 B2
(45) Date of Patent: Mar. 11, 2014

(54) N BAND FM DEMODULATION TO AID COCHLEAR HEARING IMPAIRED PERSONS

(75) Inventors: Thomas Lunner, Smorum (DK); Niels Henrik Pontoppidan, Smorum (DK)

(73) Assignee: Oticon A/S, Smorum (DK)

( * ) Notice: Subject to any disclaimer, the term of this patent is extended or adjusted under 35 U.S.C. 154(b) by 1125 days.

(21) Appl. No.: 12/599,654

(22) Filed: Nov. 10, 2009

(65) Prior Publication Data

US 2011/0249835 A1  Oct. 13, 2011

Related U.S. Application Data

(63) Continuation-in-part of application No. PCT/EP2008/065196, filed on Nov. 10, 2008.

(51) Int. Cl.
*H04R 25/00* (2006.01)

(52) U.S. Cl.
USPC .............................. 381/312; 381/23.1; 381/72

(58) Field of Classification Search
USPC .................................. 381/23.1, 312–331, 72
See application file for complete search history.

(56) References Cited

U.S. PATENT DOCUMENTS

| | | | |
|---|---|---|---|
| 4,289,935 A | 9/1981 | Zollner et al. | |
| 5,047,994 A | 9/1991 | Lenhardt et al. | |
| 6,169,813 B1 | 1/2001 | Richardson et al. | |
| 6,577,739 B1 | 6/2003 | Hurtig et al. | |
| 6,731,769 B1 | 5/2004 | Lenhardt | |
| 7,016,507 B1 * | 3/2006 | Brennan | 381/71.6 |
| 7,225,027 B2 | 5/2007 | Zeng et al. | |
| 7,340,072 B2 * | 3/2008 | Schaub | 381/312 |
| 7,936,022 B2 * | 5/2011 | Sorrells et al. | 257/368 |
| 2003/0044034 A1 | 3/2003 | Zeng et al. | |
| 2007/0203535 A1 * | 8/2007 | Zeng et al. | 607/57 |
| 2008/0123883 A1 * | 5/2008 | Blamey et al. | 381/312 |

OTHER PUBLICATIONS

Wang et al., "Real time decomposition of speech into modulated components", Journal of the Acoustical Society of America, vol. 119, No. 6, Jun. 2006.
Zeng et al. "Speech recognition with amplitude and frequency modulations", *PNAS*, vol. 12, No. 7, pp. 2293-2298(2005).
Zhou et al. "Nonlinear Feature Based Classification of Speech Under Stress", *IEEE Transactions on Speech and Audio Processing*, vol. 9, No. 3, pp. 201-216 (2001).
Swaminathan et al. "Neural coding of envelope and fine structure in noise degraded speech", *Acoustics 2008 Intl Conf. Paris*, vol. 123, No. 5, pt. 2, p. 3720 (2008).
Wang et al. "Real time decomposition of speech into modulated components", *J. Acoust. Soc. Am.*, 119 (6): pp. EL68-EL73 (2006).

* cited by examiner

*Primary Examiner* — Duc Nguyen
*Assistant Examiner* — Anita Masson
(74) *Attorney, Agent, or Firm* — Birch, Stewart, Kolasch & Birch, LLP

(57) ABSTRACT

A signal processing device comprising a signal processing unit for processing an electrical SPU-input signal comprising frequencies in the audible frequency range between a minimum frequency and a maximum frequency, and providing a processed SPU output signal. An FM to AM transformation unit transforms an FM2AM input signal originating from the SPU-input signal and comprising at least a part of the frequency range of the SPU-input signal from a frequency modulated signal to an amplitude modulated signal to provide an FM2AM output signal, which is used in the generation of the processed SPU output signal.

20 Claims, 12 Drawing Sheets

US 8,670,582 B2

N BAND FM DEMODULATION TO AID COCHLEAR HEARING IMPAIRED PERSONS

This application is a Continuation-In-Part under 35 U.S.C. §120 of Application No. PCT/EP2008/065196, filed on Nov. 10, 2008.

TECHNICAL FIELD

The present invention relates to hearing aids, particularly to the significance of modulation (e.g. AM and FM) of the acoustic signal to a user's perception of the signal. The invention relates specifically to a signal processing device, its use, and a method of operating an audio processing device.

The invention furthermore relates to a listening device, to a data processing system and to a computer readable medium.

BACKGROUND ART

Zeng et al. (2005) have argued that band limiting and compressing the FM variations to "slow" variations may be beneficial for the hearing impaired. U.S. Pat. No. 7,225,027 dealing with cochlear implants (CI) describes a signal processing strategy termed FAME (Frequency-Amplitude-Modulation-Encoding). The difference between current CI frequency encoding strategies and the FAME strategy is that previously only a fundamental frequency has been used to modulate the carrier across some or all bands in the fundamental frequency encoding strategies, while in the applications of FAME strategy in accordance to their invention, the band-specific frequency modulations (which may or may not carry fundamental frequency information) will be extracted and used to modulate the carrier frequency in the corresponding band.

In summary, the current state of art suggests that correlated FM and AM signals are produced in natural speech (c.f. Zhou, Hansen and Kaiser (2001)), and that the FM signals are important for negative signal to noise ratios for normal hearing persons, but the FM extraction may be impaired among people with cochlear impairment (c.f. Swaminathan and Heinz (2008)). However, hearing impaired can utilize the AM cues. In addition, there are inventions made for CI where the signal is made available to the CI-user by extracting FM information and presenting these by a frequency modulation carrier within a given (narrow) band.

DISCLOSURE OF INVENTION

An object of the present invention is to provide a scheme for improving a user's perception of an acoustic signal.

The foundation of the present invention is described in the following.

1. With basis in the literature, it is concluded that speech production generates both amplitude-modulated (AM) and frequency modulated (FM/Temporal Fine-Structure, TFS) cues that both carry information about the spoken message.

2. Both the FM and AM components are important in realistic listening situations.

3. Hearing impairment of cochlear origin may lead to an inability to utilize FM/TFS cues.

4. The FM/TFS cues can be made available for the hearing impaired through FM/TFS to AM transformations.

1. AM and FM Speech Modulations

Humans can engage their sound source in the larynx and their vocal tract airways in two fundamentally different ways. The first is linear source-filter coupling (as utilized in e.g. LPC (Linear Predictive Coding)), where the source frequencies are produced independently of the acoustic pressures in the airways. The second is nonlinear coupling, where the acoustic airway pressures contribute to the production of frequencies at the source. In the nonlinear case, the transglottal pressure includes a strong acoustic component, much like in woodwind instruments where the airflow through the reed is driven by acoustic pressures of the instrument bore, or in brass instrument playing, where the lip flow is driven by the acoustic pressures in the brass tube (Barney et al. (1999); Shadle et al. (1999)). There is much experimental and theoretical evidence for the existence of the non-linear coupling showing amplitude modulation (AM) and frequency modulation (FM) in speech resonance signals, which make the amplitude and frequency of the resonance vary instantaneously within a pitch period (McLaughlin & Maragos (2006), Maragos et al. (1993a), Teager & Teager 1990). Motivated by this evidence, Maragos et al. (1993a) proposed to model each speech resonance with an AM-FM signal and the total speech signal as a superposition of such AM-FM signals.

2. Both FM and AM Components are Important in Realistic Situations

Recent research has been devoted to explore the contributions of envelope/AM and fine-structure FM modulations of speech. Zeng et al. (2005) summarizes some of the research in the following statements emphasizing the importance of AM and FM in different acoustic situations:

- AM (where FM cues are removed by e.g. noise vocoders) from a limited number of bands sufficient for speech recognition in quiet.
- FM significantly enhances speech recognition in noise, as well as speaker and tone recognition.
- FM is particularly critical for speech recognition with a competing voice.
- AM and FM provide independent, complementary contributions to support robust speech recognition under realistic listening situations.

3. Hearing Impairment and TFS/FM

Swaminathan and Heinz (2008) have evaluated neural cross correlation coefficient (CCC) metrics to quantify envelope (ENV) and TFS/FM coding in auditory nerve responses. Their analyses reveal that CCC ENV>CCC TFS for positive SNRs, whereas CCC TFS>CCC ENV for negative SNRs, indicating a switch of emphasis between ENV and TFS cues depending on SNR.

Emerging evidence shows that persons with hearing impairment of cochlear origin have difficulties to utilize the TFS/FM cues (e.g. Lorenzi et al. (2006), Hopkins & Moore (2007), Hopkins et al. (2008)), while AM/envelope cues seem to be unaffected by the hearing impairment. It is argued that subjects with moderate cochlear hearing loss have a limited ability to use FM/TFS information, especially for medium and high frequencies. This may explain some of the speech perception deficits found for such subjects, especially the reduced ability to take advantage of temporal dips in a competing background.

The Hilbert Transform allows a real signal to be transformed into an analytical signal, $$\tilde{x}(t) = x(t) + jH(x(t))$$

$$H(x(t)) = \int_{-\infty}^{\infty} \frac{x(\tau)}{\pi(t-\tau)} d\tau$$

where $|\tilde{x}(t)|$ is the envelope of the signal x(t) and $<\tilde{x}(t)$ is the phase of the signal. The envelope can be extracted in other ways, e.g. by rectification and low-pass filtering as in Zeng et al (2005). Both frequency modulation and temporal fine structure are defined from the phase. Temporal fine structure term is often used as a synonym of the phase. The link to frequency modulation is through the instantaneous frequency (time derivative of the phase). Broad picture details and special cases etc. are well known to those skilled in the art. Strictly speaking, all phase signals can be generated through a frequency modulation function due to the link through the time derivative. It is the intention in the present context that the term frequency modulation includes temporal fine structure (phase) related modulation.

4. FM to AM Transformation

The present invention is borne by the acknowledgment that voices carry information that is spread out over the whole frequency region of speech, and that speech FM components may carry redundant information because they stem from the same generating origin. This is probably used by nature for noise resistance in situations with competing signals/voices, where the top-down processing of the brain can choose which frequency regions to rely upon to allocate grouped cues to a given object. However, band-specific FM/AM variations are also possible.

The invention acknowledges that intact FM demodulation abilities seem to be necessary for normal hearing. There is evidence that FM to AM demodulation takes place in connection with normal cochlear processing. Both AM and FM represented as relatively independent amplitude information in auditory steady state brainstem responses, ASSR (John et al. (2001); Picton et al. (2002)) for normal hearing but the FM representation is minimal for hearing impaired. Furthermore, Ghitza (2001) suggests that (normally) steep auditory filter band flanks may act as FM to AM conversion/demodulation. Hearing impairment will give less steep filter flanks and thereby less FM to AM decoding abilities.

Furthermore, there is ample evidence that the individual FM-components in the harmonic complexes produced in voiced speech are highly correlated (Ru et al., 2003), since they originate from the same non-linearity when produced. For example, the Spectral Band Replication technique (Liljeryd et al. (1998); Liljeryd et al. (2001)) utilizes this when copying frequency modulated information (FM/TFS) from one band to another.

In addition, the $F_0$-range ($F_0$ being a fundamental frequency of the particular voice signal) of a voice may for example range from 150-250 Hz (with corresponding variation for the higher order harmonics). This may be assumed to be a FM-signal with a (fixed) carrier frequency of 200 Hz and with FM variations (i.e. the message) of +/−0.25 $F_0$.

Phase locked loops are explained in e.g. Wang and Kumaresan (2006). One active component in the normal healthy cochlea is the outer hair cell (OHC) acting as a voltage controlled oscillator (VCO); Rabbitt et al. (2005), Hudspeth et al. (2005), Libermann et al. (2002) and including the active component in a feedback loop (Geisler (1991)).

One embodiment of the invention utilizes the fact that the normal healthy cochlea includes active (and vulnerable) components that here are implemented as components of a phase locked loop circuit (PLL) including a VCO. For example it has been shown that with a sine input of a healthy cochlea the vibration pattern of the OHC having a characteristic frequency close to the sine input, the OHC vibrates with the same frequency. However, at the site of the inner hair cell (IHC, which codes the vibration to neural input) the vibration frequency is the double compared to the OHC site (Fridberger et al. (2006)). This is consistent with a suggestion that the OHC acting as a VCO in a PLL similar to Wang and Kumaresan (2006), and the IHC site being the product (demodulation) of the input signal and a VCO signal (i.e. producing a DC component and a sine with the double frequency).

Furthermore, it can be interpreted that the normal healthy cochlea has the properties of a number of differently frequency tuned phase locked loops along the basilar membrane. The normal cochlear function shows similarities to phase-locked loops such as a 'capture effect' (Miller et al. (1997)) typical to phase locked loop circuits; the capture effect is lost with a cochlear damage, where the active component is lost. Furthermore, normal hearing subject's FM detection shows robustness to AM modulation (Moore & Skrodzka (2002)), a property which is typical for phase-locked loop circuits. A cochlear damage reduces the subject's FM detection robustness to AM modulations (Moore & Skrodzka (2002)).

The invention utilizes the fact that the phase-locked loop behavior is lost in cochlear damage to restore this by artificial signal processing phase locked loops.

Objects of the invention are achieved by the invention described in the accompanying claims and as described in the following.

A Signal Processing Device

An object of the invention is achieved by a signal processing device comprising a signal processing unit (SPU) for processing an electrical (SPU-) input signal, termed the SPU-input signal, comprising frequencies in the audible frequency range between a minimum frequency and a maximum frequency, and providing a processed (SPU) output signal, termed the SPU output signal, wherein an FM to AM transformation unit for transforming an (FM2AM) input signal originating from the SPU-input signal, termed the FM2AM input signal, the FM2AM input signal comprising at least a part of the frequency range of the SPU-input signal, from a frequency modulated signal to an amplitude modulated signal to provide an (FM2AM) output signal, termed the FM2AM output signal, which is used in the generation of the processed SPU output signal.

This has the advantage of providing an improved perception by a hearing impaired user of an input sound.

It is to be understood that the electrical input signal e.g. is an electrical signal representing a time varying audio signal comprising amplitude modulated as well as frequency modulated components, such as e.g. an audio signal from a human voice, e.g. speech, singing or other human utterances.

In the present context, the abbreviations SPU (signal processing unit) and FM2AM (FM-to-AM) in relation to input and output signals are used as a means of reference to imply their relation to the mentioned units ('signal processing device' and 'FM to AM transformation unit', respectively) as an alternative to 'first' and 'second'.

In the present application the terms 'frequency range' and 'frequency band' and 'frequency channel' (or simply 'range', 'band' or 'channel') are used interchangeably to indicate an interval of frequencies from a minimum to a maximum frequency. The frequency ranges or bands can e.g. be of equal width, but need not be. They can be overlapping or non-overlapping. The total frequency range considered in the present application is the human auditory frequency range, e.g. 20 Hz to 25 kHz. The relevant frequency range for signal processing is typically a sub-range thereof. The number of frequency bands that the input signal is split into can be any practical number N, such as 2 or more, e.g. 8 or 16 or 128, or more.

It should be understood that in addition to or as an alternative to 'transformation of a frequency modulated signal to an amplitude modulated signal', the information in the amplitude modulated signal may originate from the transformation of a phase modulated (PM) signal or of a signal comprising temporal fine structure (TFS) to an amplitude modulated signal. Preferably, the modulation function extracted from the frequency modulated signal is used to alter the envelope of a 'constant envelope signal' (e.g. a carrier signal), in order to achieve the 'FM2AM functionality'. In other words, preferably, the FM2AM output signal is used to amplitude modulate an input signal with a constant envelope. Or alternatively worded, the amplitude modulation applied to the (SPU-)input signal (overall or in a given band, and resulting in the SPU output signal) is based on the 'transformation of a frequency modulated signal to an amplitude modulated signal' extracted from the input signal (overall or in a given band). Preferably, the information contained in the frequency modulation of the electric input signal is applied to the input signal as amplitude modulation. The resulting amplitude modulated signal is used in the further processing or presented to a user via an appropriate output transducer. This signal contains information that is otherwise not perceived by a hearing impaired person.

In an embodiment, the signal processing device comprises a time to time-frequency transformation unit providing a time varying representation of the SPU-input signal in a number of frequency ranges. In an embodiment, the signal processing device comprises a filter bank for splitting the SPU-input signal in a number of frequency bands. Alternatively, the signal processing device is adapted to receive an SPU-input signal arranged in a time varying representation in a number of frequency ranges.

In an embodiment, the signal processing device comprises an AM-demodulation unit for extracting an amplitude modulation function am(t) of the at least one signal originating from the SPU-input $x(t)$, e.g. from a signal comprising the total frequency range considered by the application (e.g. the SPU). In an embodiment, the signal processing device comprises an AM-demodulation unit for extracting an amplitude modulation function $am_n(t)$ of the at least one signal originating from the SPU-input signal, n being a frequency range index, n=1, 2, ..., N.

In an embodiment, the signal processing device comprises an FM-demodulation unit for extracting a frequency modulation function fm(t) of the at least one signal originating from the SPU-input $x(t)$, e.g. from a signal comprising the total frequency range considered by the application. In an embodiment, the signal processing device comprises an FM-demodulation unit for extracting a frequency modulation function $fm_n(t)$ of the at least one signal originating from SPU-input signal, n being a frequency range index, n=1, 2, ..., N.

The term 'function' is used here to indicate the importance of the particular functional dependence on an independent parameter (here e.g. time, t, e.g. $am_n(t)$, $fm_n(t)$). The extracted 'functions' can likewise be treated as 'signals'. Typically the mentioned functions are information signals or modulated signals that are extracted from or modulated onto a carrier or otherwise combinable with another electrical signal. An index n on a function, e.g. $am_n$, $fm_n$, $FM2AM_n$, etc., is intended to indicate that the function in question relates to the frequency band or range n.

In an embodiment, the signal processing device is adapted to provide that the FM to AM transformation is performed within the same band so that the original signal (e.g. the SPU-input signal) and the FM2AM signal are located within the same band, p=n. This has the effect/advantage of providing a local transformation of otherwise inaccessible information presented to the hearing impaired user in the same frequency range.

Alternatively, the FM2AM information from one band can be transposed to another band. In an embodiment, the signal processing device is adapted to provide that the FM to AM transformation of a signal originating from the SPU-input signal and comprising a frequency range p is based on the frequency modulation function $fm_n(t)$ extracted from a signal comprising a frequency range n, where p≠n. Thereby the typical harmonicity of the input signal across several frequency ranges is utilized, c.f. Lunner (2007). In an embodiment, the SNR of the SPU-input signal in a given frequency range or band may determine which band to copy to and from. E.g., if the SNR in a band is below a certain threshold SNR, then the algorithm selects another band with a better SNR and copies from that.

In an embodiment, the signal processing device comprises a phase locked loop circuit for generating the amplitude modulation function $am_n(t)$ of the at least one signal originating from the SPU-input signal (c.f. e.g. Wang and Kumaresan, 2006).

In an embodiment, the AM-demodulation unit is adapted to provide that the amplitude modulation function $am_n(t)$ of the at least one signal originating from the SPU-input signal is generated by extracting the envelope of the channel signal.

In an embodiment, the signal processing device comprises a phase locked loop circuit for generating the frequency modulation function $fm_n(t)$ of the at least one signal originating from the SPU-input signal.

In an embodiment, the FM-demodulation unit is adapted to provide that the frequency modulation function $fm_n(t)$ of the at least one signal originating from the SPU-input signal is generated by extracting the instantaneous frequency of the channel signal.

In an embodiment, the signal processing device comprises a carrier unit for providing a sinusoidal $c_n$ with a carrier frequency within the frequency range n. In an embodiment, the signal processing device comprises a carrier unit for providing a sinusoidal $c_n$ with a carrier frequency equivalent to the middle of a frequency range n and amplitude $A_n$ and an AM modulator for amplitude modulating the sinusoidal $c_n$ with the demodulated FM signal $fm_n(t)$ thereby providing the FM to AM transformation ($FM2AM_n$) in frequency range n.

In an embodiment, the signal processing device comprises an AM modulator for amplitude modulating the SPU-input signal $x_n$ of the frequency range or channel n with the demodulated FM signal $fm_n(t)$, thereby providing the FM to AM transformation and the FM2AM output signal ($FM2AM_n$) in frequency range n.

In an embodiment, the signal processing device comprises a combiner unit (e.g. termed AM combiner below) for combining the at least one signal (such as two of, three of or all of the signals) originating from the SPU-input signal, the amplitude modulation function, the frequency modulation function and/or the FM2AM signal with weights and providing a weighted amplitude modulation function. In an embodiment, the combiner unit provides as an output signal a linear combination of the input signals $SUM(w_i * X_i)$ where $w_i$ are the weights and i=1, 2, ..., Q, where Q is the number of input signals to the combiner unit. In an embodiment, the output signal of the combiner unit for a given band n is $w_{1n}*X_n + w_{2n}*am_n + w_{3n}*fm_n + w_{4n}*FM2AM_n$, where the input signals ($X_i$) $x_n$, $am_n$, $fm_n$ and $FM2AM_n$ have their previous meaning for the frequency range n. In an embodiment, one or more of the weights $w_i$ ($w_{in}$) may be zero. In an embodiment, the combiner unit provides an output signal comprising a multiplication of the input signals $X_i$ of the form $PROD(a_i + X_i)$, where $a_i$ is a constant, e.g. 1. In a band split notation the combiner output for frequency range n can be written in the following way: $PROD((a_{n1}+wn_{1b} X_n)(a_{n2}+b_{n2} am_n)(a_{n3}+b_{n3}$ $fm_n)(a_{n4}+b_{n4} FM2AM_n))$, where the input signals have their previous meanings for the frequency range n (n=1, 2, ..., N).

In an embodiment, the signal processing device comprises a combiner unit for combining the extracted amplitude modulation function $am_n(t)$ and the FM2AM transformed signal of the corresponding frequency range ($FM2AM_n(t)$) with weights and providing a weighted amplitude modulation function.

In an embodiment, the signal processing device comprises a combiner unit for combining the at least one signal originating from the SPU-input signal x and the FM2AM transformed signal with weights and providing a weighted amplitude modulation function.

In an embodiment, the FM2AM transformed signal is the frequency modulation function fm(t) of the SPU-input signal. In an embodiment, the FM2AM transformed signal $FM2AM_n(t)$ of a given frequency range n is equal to the frequency modulation function $fm_n(t)$ of the at least one signal $x_n$ originating from the SPU-input signal x.

In an embodiment, the signal processing device comprises a combiner unit for combining the at least one signal $x_n$ originating from the SPU-input signal and the frequency modulation function $fm_n(t)$ of the corresponding frequency range with weights and providing a weighted amplitude modulation function.

In an embodiment, the signal processing device comprises an SQE-unit for evaluating the signal quality of the SPU-input signal, e.g. its signal to noise ratio (SNR), a bit error rate, or the like. In an embodiment, the signal processing device is adapted to receive a measure of the signal quality of the the SPU-input signal. In an embodiment, the combiner unit is adapted to control the weights in dependence of the signal quality, e.g. the signal to noise ratio (SNR) of the SPU-input signal.

In an embodiment, the signal processing device is adapted to provide that the weight of the FM2AM signal in a given frequency range increases with decreasing SNR of the SPU-input signal in that frequency range. In an embodiment, the signal processing device is adapted to provide that in a range between a medium SNR, $SNR_{med}$, and a low SNR, $SNR_{low}$, the provided weighted amplitude modulation function is solely based on the FM2AM function. In an embodiment, the weight of the original signal (the SPU-input signal) is zero for negative SNRs.

In an embodiment, the AM combiner is adapted to select or combine from three sources of amplitude modulation, 1. the provided AM function am(t), 2. the provided FM function fm(t), and 3. the FM-to-AM converted function FM2AM(t). In an embodiment, the AM combiner is adapted to select the AM function (am(t)) in situations with a relatively high SNR ($SNR>SNR_{high}$, where the AM function is believed to be good enough for the user to utilize). In an embodiment, the AM combiner is adapted to combine the AM (am(t)) and FM (FM2AM(t)) functions in situations where the SNR is lower ($SNR_{high}>SNR>SNR_{med}$, where the AM function is believed NOT to be sufficiently good for the user to rely on ALONE). In an embodiment, the AM combiner is adapted to select the FM function (FM2AM(t)) and discard the AM function (am(t)) completely, if the SNR is even worse ($SNR_{med}>SNR>SNR_{low}$, where the AM function is believed to be buried in noise). In an embodiment, the AM combiner is adapted to additionally select or combine with the channel signal x. In an embodiment, the AM combiner is adapted to select the channel signal x possibly attenuated or silence, if the FM function (FM2AM(t)) is estimated to be so distorted that it cannot be utilized by a hearing impaired user ($SNR_{low}>SNR$).

In an embodiment, the weighted amplitude modulation function in a given frequency range n is used (directly or as a basis for a further processed, enhanced signal) to present to a user in that frequency range, whereby an improved perception of the input (e.g. speech) signal is provided.

One way to implement the FM2AM conversion is use the FM function fm(t) directly to amplitude modulate a pure tone (at the centre of the channel). In an embodiment, the signal processing device comprises a carrier unit for providing a sinusoidal $c_n$ with a carrier frequency in, such as equivalent to the middle of, a frequency range n, and an AM modulator for amplitude modulating the sinusoidal with the weighted amplitude modulation function creating an amplitude modulated weighted output signal in that frequency range. This has the effect that the previously inaccessible information carried in the frequency modulation function is made usable as amplitude modulated information for the user.

A second approach is use the FM function directly to amplitude modulate the channel signal $x_n$ itself. In an embodiment, the signal processing device comprises an AM modulator for amplitude modulating the SPU-input signal $x_n$ in a frequency range n with the weighted amplitude modulation function creating an amplitude modulated weighted output signal in that frequency range.

A third approach to implement the FM2AM conversion is to extract the amplitude modulation that a normal cochlea, as suggested by Ghitza (2001), could extract from such FM signal. In that case the FM function fm(t) is used to modulate a pure tone at the centre frequency $f_c$ of the band, and the output FM(t) of the FM modulator is fed through an ERB-wide filter centered on the channel centre frequency (ERB=Equivalent Rectangular bandwidth). The envelope of the filter output is an AM function created as a function of the FM function (cf. e.g. FIG. 6).

A fourth approach can easily be deducted from the DESA-1a approximation to Teager's Energy Operator (Maragos, Kaiser, and Quatieri (1993b)) (cf. e.g. FIG. 10).

Preferably, the amplitude modulated weighted output signal in a given frequency range n is used (directly or as a basis for a further processed, enhanced signal) to present to a user in that frequency range, whereby an improved perception of the input (e.g. speech) signal is provided.

When the FM function is extracted in a particular frequency range or band of the SPU-input signal it is possible to modulate the centre frequency of the band with that FM function in order to recreate the frequency modulation, especially after enhancement of the FM function as in the FAME processing (Zeng et al. (2005)).

In an embodiment, the signal processing device comprises an FT-unit for providing a (time-)frequency to time (FT) transformation of a signal originating from the FM2AM signal(s) to generate an SPU-output signal in the time domain.

In an embodiment, the signal processing device is adapted to provide that the SPU-output signal is appropriate for driving a receiver of a normal listening device, or an electrode of a cochlear implant, or a vibrator of a bone conducting device.

Use of a Signal Processing Device

In an aspect, use of a signal processing device as described above, in the detailed description of 'mode(s) for carrying out the invention' and in the claims is moreover provided by the present invention. In an embodiment, use is provided in a listening device, such as a hearing aid, e.g. a hearing instrument, or a head set, or a headphone or an active ear protection device.

A Listening Device Comprising a Signal Processing Device

In a further aspect, a listening device is provided, the listening device comprising a signal processing device as described above, in the detailed description of 'mode(s) for carrying out the invention' and in the claims AND an input transducer for converting an input sound to an electrical input signal, wherein the electrical SPU-input signal originates from the electrical input signal from the input transducer.

In the present context, the term a second signal 'originates from' a first signal is taken to mean that the second signal is equal to or derivable (or predictable) from the first signal, e.g. in the second signal is a processed version of the first signal and/or comprises a part of the frequency range of the first signal.

In an embodiment, the listening device comprises an output transducer for converting a processed electric output signal to a signal representative of sound for a user, wherein the processed electric output signal originates from the FM2AM output signal.

In an embodiment, the output transducer is a receiver (e.g. for a hearing instrument or any other loudspeaker of an audio processing system) or an electrode for a cochlear implant or an electro-mechanical transducer for a bone conducting device.

In an embodiment, the listening device comprises a hearing instrument, a headset, a headphone or an active ear protection device or a combination thereof.

A Method of Operating a Listening Device

A method of operating an audio processing device comprising processing an SPU-input signal according to a user's needs, the SPU-input signal comprising frequencies in a range between a minimum frequency and a maximum frequency, and providing a processed SPU output signal, is furthermore provided by the present invention, wherein the processing of an SPU-input signal according to a user's needs comprises providing an FM to AM transformation of at least one signal originating from the SPU-input signal and comprising at least a part of the frequency range of the SPU-input signal and providing an FM to AM (FM2AM) transformed signal.

It is intended that the structural features of the device described above, in the detailed description of 'mode(s) for carrying out the invention' and in the claims can be combined with the method, when appropriately substituted by a corresponding process feature. Embodiments of the method have the same advantages as the corresponding device.

In a particular embodiment, the processing of an SPU-input signal according to a user's needs comprises that the FM2AM transformed signal is used to amplitude modulate a constant envelope input signal to provide a resulting amplitude modulated signal, which is used as a basis for the processed SPU output signal.

Preferably, the information contained in the frequency modulation of the electric SPU-input signal is applied to the signal as amplitude modulation, which is used as a basis for the processed SPU output signal.

Preferably, the FM2AM transformed signal is used to amplitude modulate a constant envelope input signal (e.g. a carrier) to provide a resulting amplitude modulated signal (the processed SPU output signal). The resulting amplitude modulated signal is used in the further processing or presented to a user via an appropriate output transducer. This signal contains information that is otherwise not perceived by a hearing impaired person.

In an embodiment, the method comprises converting an input sound to an electrical input signal, and wherein the SPU-input signal originates from the electrical input signal. In an embodiment, the method comprises receiving the SPU-input signal from a wired or wireless connection.

In an embodiment, the method comprises generating an output stimulus representative of the input sound to a user based on a signal originating from the SPU-output signal.

In an embodiment, the method comprises a time to frequency transformation providing a representation of the SPU-input signal in a number of frequency ranges.

In an embodiment, the method further comprises providing a time to time-frequency transformation providing a time varying representation of the SPU-input signal in a number of frequency ranges.

In an embodiment of the invention, the electrical input signal is split into N (band limited) FM signals, which are processed individually into a form which the hearing impaired can utilize, that is to convert/demodulate the band limited FM signals into AM signals within the same or another band. This can for example be made by taking the FM-demodulated signal, and modulating a sinusoidal (tone-vocoding) with a carrier frequency equivalent to the middle of the band and amplitude modulated with the decoded FM signal.

In an embodiment, the method comprises extracting an amplitude modulation function $am_n(t)$ of the at least one signal originating from the SPU-input signal, n being a frequency range index.

In an embodiment, the method comprises extracting a frequency modulation function $fm_n(t)$ of the at least one signal originating from SPU-input signal, n being a frequency range index.

In an embodiment, the FM to AM transformation of a signal $x_p$ originating from the SPU-input signal and comprising a frequency range p is based on the frequency modulation function $fm_n(t)$ extracted from a signal $x_n$ comprising a frequency range n.

In an embodiment, the FM to AM transformation is performed within the same band so that the original and the FM2AM signal are located within the same band, p=n. This has the effect/advantage of providing a local transformation of otherwise inaccessible information presented to the hearing impaired user in the same frequency range. Alternatively, the FM2AM information from one band transposed to another band is used. In an embodiment, the FM to AM transformation is performed in one frequency range p and copied to another frequency range n, p≠n. Thereby the typical harmonicity of the input signal across several frequency ranges is utilized c.f. Lunner (2007). In an embodiment, the SNR of the SPU-input signal in a given frequency range or band may determine which band to copy to and from. E.g. if the SNR in a band is below a certain threshold SNR, then the algorithm selects another band with a better SNR and copies from that.

In an embodiment, the amplitude modulation function $am_n(t)$ of the at least one signal originating from the SPU-input signal is generated by a phase locked loop circuit (c.f. Wang and Kumaresan (2006)). In an embodiment, the amplitude modulation function $am_n(t)$ of the at least one signal originating from the SPU-input signal is generated by extracting the envelope of the channel signal.

In an embodiment, the frequency modulation function $fm_n(t)$ of the at least one signal originating from the SPU-input signal is generated by a phase locked loop circuit. In an embodiment, the frequency modulation function $fm_n(t)$ of the at least one signal originating from the SPU-input signal is generated by extracting the instantaneous frequency of the channel signal.

In an embodiment, the method comprises generating a sinusoidal with a carrier frequency equivalent to the middle of a frequency range n and amplitude modulating the sinusoidal with the demodulated FM signal $fm_n(t)$ thereby providing the FM to AM transformation ($FM2AM_n(t)$) in frequency range n.

In an embodiment, the method comprises combining the at least one signal (such as one or more or all of the band specific signals $x_n$) originating from the SPU-input signal x, the amplitude modulation function am(t) ($am_n(t)$), the frequency modulation function fm(t) ($fm_n(t)$) and/or the FM2AM transformed signal FM2AM(t) ($FM2AM_n(t)$) with weights and providing a weighted amplitude modulation function.

In an embodiment, the at least one signal originating from the SPU-input signal and comprising at least a part of the frequency range of the SPU-input signal and the FM2AM transformed signal are combined with weights and providing a weighted amplitude modulation function (possibly individually processed in a number of bands).

In an embodiment, the extracted amplitude modulation function $am_n(t)$ and the FM2AM transformed signal $FM2AM_n(t)$ of the corresponding frequency range are combined with weights and providing a weighted amplitude modulation function.

In an embodiment, the FM2AM transformed signal $FM2AM_n(t)$ of a frequency range n is equal to the frequency modulation function $fm_n(t)$ of the at least one signal $x_n$ originating from the SPU-input signal.

In an embodiment, the weighted amplitude modulation function (either full band or in a given frequency range n) is used (directly or as a basis for a further processed, enhanced signal) as the processed SPU output signal to present to a user (either in the full frequency range or in the frequency range in question), whereby an improved perception of the SPU-input (e.g. speech) signal is provided.

In an embodiment, the weights are controlled in dependence of the signal to noise ratio (SNR) of the SPU-input signal. In an embodiment, the weight of the FM2AM signal in a given frequency range increases with decreasing SNR of the SPU-input signal in that frequency. In an embodiment, the weighted amplitude modulation function is solely based on the FM2AM function in a range between a medium SNR, $SNR_{med}$, and a low SNR, $SNR_{low}$. In an embodiment, the weight of the original signal (the SPU-input signal) is zero for negative SNRs.

In an embodiment, the method comprises generating a sinusoidal with a carrier frequency equivalent to the middle of a frequency range n and amplitude modulating the sinusoidal with the weighted amplitude modulation function creating an amplitude modulated weighted output signal in frequency range n. This has the effect that the previously inaccessible information carried in the frequency modulation function is made usable as amplitude modulated information for the user.

Preferably, the amplitude modulated weighted output signal (full band or in a given frequency range n) is used (directly or as a basis for a further processed, enhanced signal) as the processed SPU output signal to present to a user (in the full frequency range or in the frequency range in question), whereby an improved perception of the SPU-input (e.g. speech) signal is provided.

When the FM function is extracted in a particular frequency range or band of the SPU-input signal it is possible to modulate the centre frequency of the band with that FM function in order to recreate the frequency modulation, especially after enhancement of the FM function as in the FAME processing (Zeng et al. 2005).

FM2AM-Conversion:

One way to implement the FM2AM conversion is use the FM function directly to amplitude modulate a pure tone (at the centre of the channel). A second approach is use the FM function directly to amplitude modulate the channel signal itself. A third approach is to extract the amplitude modulation that a normal cochlea, as suggested by Ghitza (2001), could extract from such FM signal. In that case the FM function is used to modulate a pure tone at the centre frequency of the band or the channel signal itself, and the output of the FM modulator is fed through an ERB-wide filter centered on the channel centre frequency (ERB=Equivalent Rectangular bandwidth). The envelope of the filter output is an AM function created as a function of the FM function. A fourth approach can easily be deducted from the DESA-1a approximation to Teager's Energy Operator (c.f. Maragos, Kaiser, and Quatieri (1993b)).

In an embodiment, the method comprises providing a time-frequency to time transformation of a signal originating from the FM2AM signal(s) to generate an SPU-output signal in the time domain.

In an embodiment, the output stimulus is adapted to be appropriate for a hearing aid comprising a receiver of a normal listening device, or for an electrode of a cochlear implant or for a vibrator of a bone conducting device.

In an embodiment, the method comprises a frequency to time (FT) transformation of a signal originating from the FM2AM signal(s) and generating an SPU-output signal in the time domain.

A Data Processing System

In a further aspect, a data processing system is provided, the data processing system comprising a processor and program code means for causing the processor to perform at least some of the steps of the method described above, in the detailed description of 'mode(s) for carrying out the invention' and in the claims. In an embodiment, the program code means at least comprise some of the steps such as a majority of the steps such as all of the steps of the method. In an embodiment, the data processing system form part of a signal processing device as described above, in the detailed description of 'mode(s) for carrying out the invention' and in the claims.

A Computer Readable Medium

In a further aspect, a computer readable medium is provided, the computer readable medium storing a computer program comprising program code means for causing a data processing system to perform at least some of the steps of the method described above, in the detailed description of 'mode(s) for carrying out the invention' and in the claims, when said computer program is executed on the data processing system. In an embodiment, the program code means at least comprise some of the steps such as a majority of the steps such as all of the steps of the method.

Further objects of the invention are achieved by the embodiments defined in the dependent claims and in the detailed description of the invention.

As used herein, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements maybe present, unless expressly stated otherwise. Furthermore, "connected" or "coupled" as used herein may include wirelessly connected or coupled. As used herein, the term "and/or" includes any and all combinations of one or more of the associated listed items. The steps of any method disclosed herein do not have to be performed in the exact order disclosed, unless expressly stated otherwise.

BRIEF DESCRIPTION OF DRAWINGS

The invention will be explained more fully below in connection with a preferred embodiment and with reference to the drawings in which.

The figures are schematic and simplified for clarity, and they just show details which are essential to the understanding of the invention, while other details are left out.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

MODE(S) FOR CARRYING OUT THE INVENTION

Figure 12:
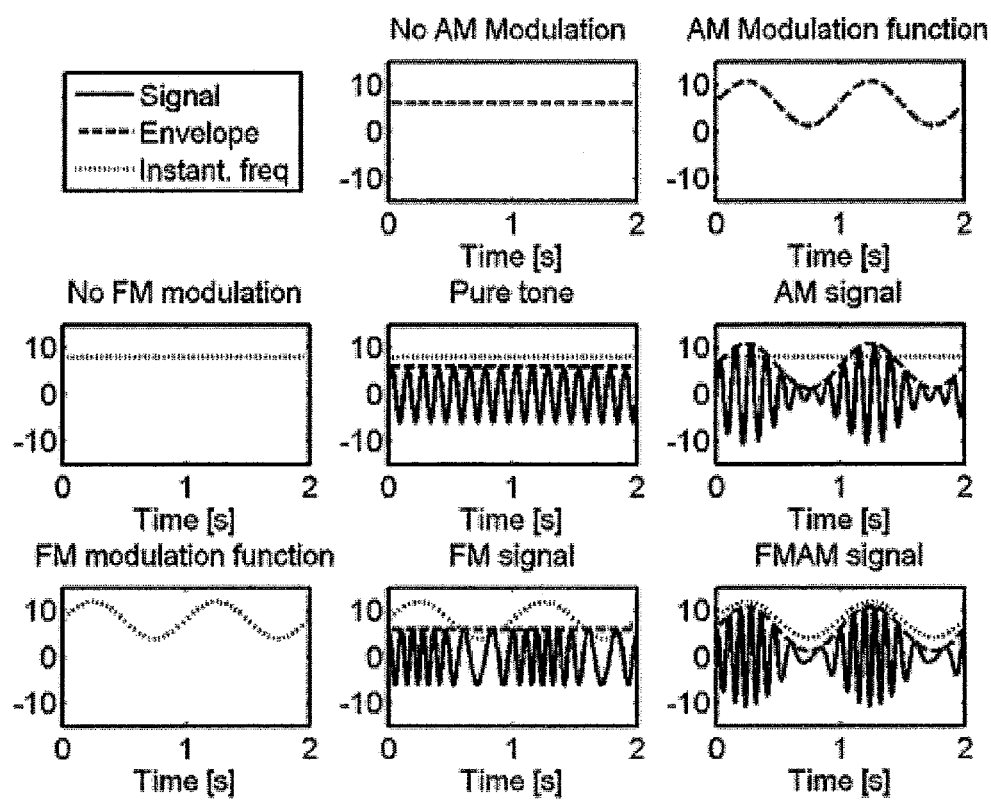
FIG. 12 shows different basic components of an AM, an FM and an AM-FM signal.

A speech signal comprises amplitude-modulated (AM) as well as frequency modulated (FM) cues that both carry information about the spoken message. FIG. 12 illustrates different basic components of an AM, an FM and an AM-FM signal. FIG. 12 contains 8 small diagrams with amplitude vs. time waveforms and a legend. The 4 diagrams in the lower right part of FIG. 12 can be thought of as a 2×2 matrix with 4 matrix-elements, the rows representing 'No FM' and 'FM', respectively, and the columns representing 'No AM' and 'AM', respectively. The lower right four (2×2) graphs of the matrix show simple time dependent signal waveforms exemplifying the 4 combinations. The lower right element thus shows a simple example of an FMAM(t) signal comprising AM as well as FM components.

The signals shown in the second (middle) column have no AM modulation, whereas the signals in the third (rightmost) column share the same AM modulation (as indicated by the dashed curves of the diagrams in the top row). The signals in the second (middle) row have no FM modulation, whereas the signals in the third (bottom) row share the same FM modulation (as illustrated by the dotted curves of the diagrams in the first (leftmost) column). The AM and FM signals show how more or less the same information (the AM and FM modulation functions (am(t), fm(t), respectively) shown in the top row and leftmost column, respectively) can be conveyed in different manners, while the FMAM signal shows a signal, where the information is conveyed through the AM and FM components at the same time. The offset between the AM and FM modulation function is arbitrary and here specifically selected to ease printing.

Figure 13:
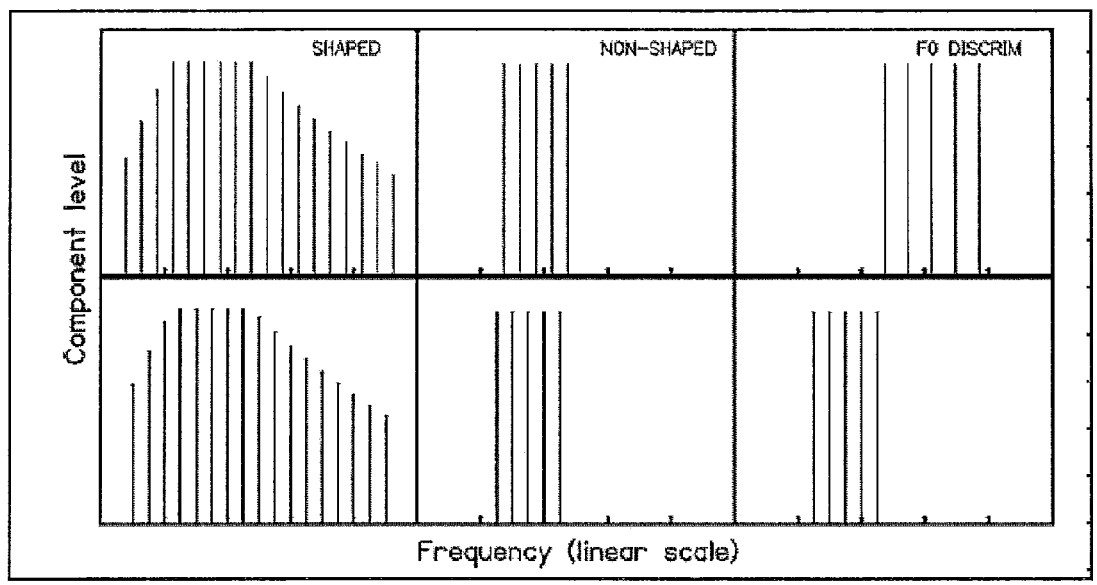
FIG. 13 is a copy of FIG. 1 of Hopkins and Moore (2007), showing the level and frequency location of the pure tones in the TFS1 test stimuli.

The TFS1 test proposed by Hopkins and Moore (2007) uses stimuli where the difference between the reference and shifted stimuli are believed to be conveyed by the fine structure. The component levels of the stimuli are the "SHAPED" stimuli shown in FIG. 13 (leftmost stimuli of FIG. 13). While normal hearing listeners are able to complete the adaptive procedure providing a discrimination threshold in terms of a frequency translation measured in hertz, the hearing impaired cannot reliably identify the translated stimuli even at the maximal frequency shift.

Figure 14:
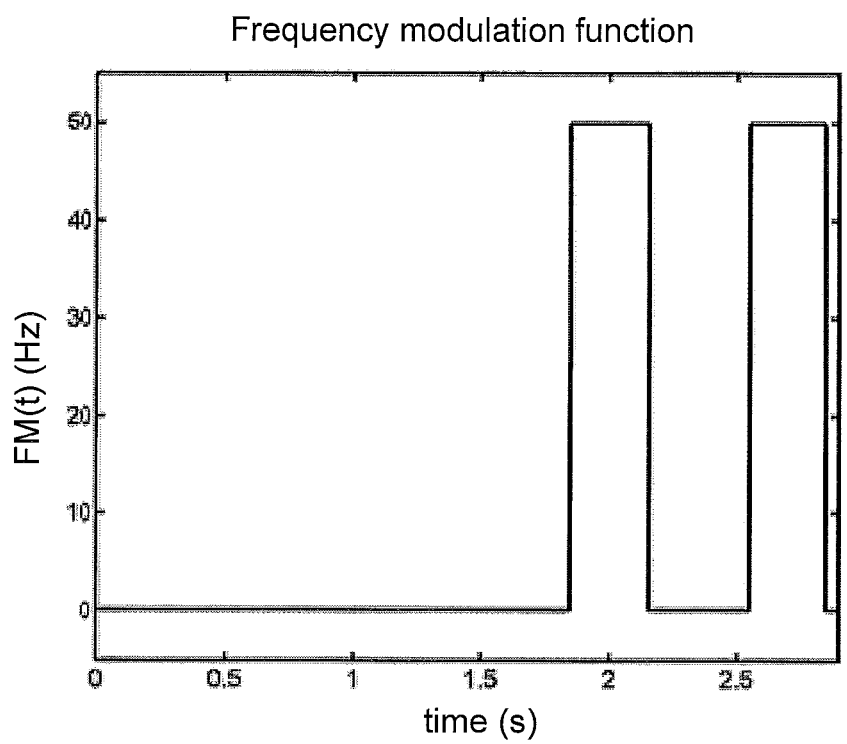
FIG. 14 shows the frequency modulation function for the TFS1 test stimuli fm(t) [0-50 Hz] vs. time [0-3 s]

For a specific configuration of the TFS1 test, the shifted stimuli could be considered to be the reference stimuli frequency shifted by 50 Hz, i.e. the frequency-modulation function depicted in FIG. 14.

Figure 15:
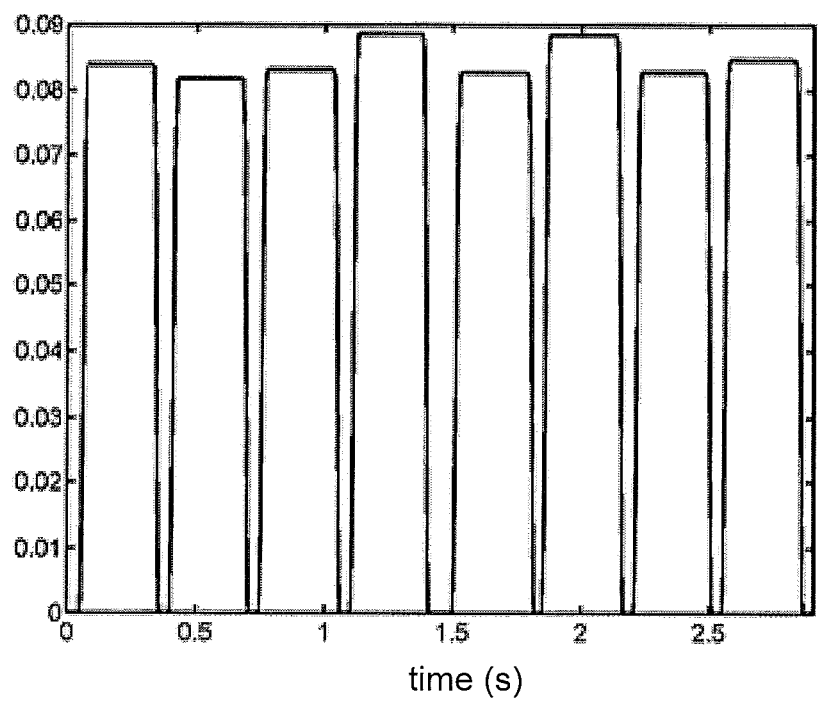
FIG. 15 shows the envelope of the TFS1 test stimuli [0-0.09] (strength or amplitude) vs. time [0-3 s]

The problem is believed to be that the hearing impaired cannot access the frequency-modulation function depicted in FIG. 14, but only the rather non-informative envelope depicted in FIG. 15. The following presents a few examples where the TFS1 stimuli are processed with the FM2AM algorithm in order to enable the hearing impaired in discriminating between the reference and the shifted stimuli.

Figure 16:
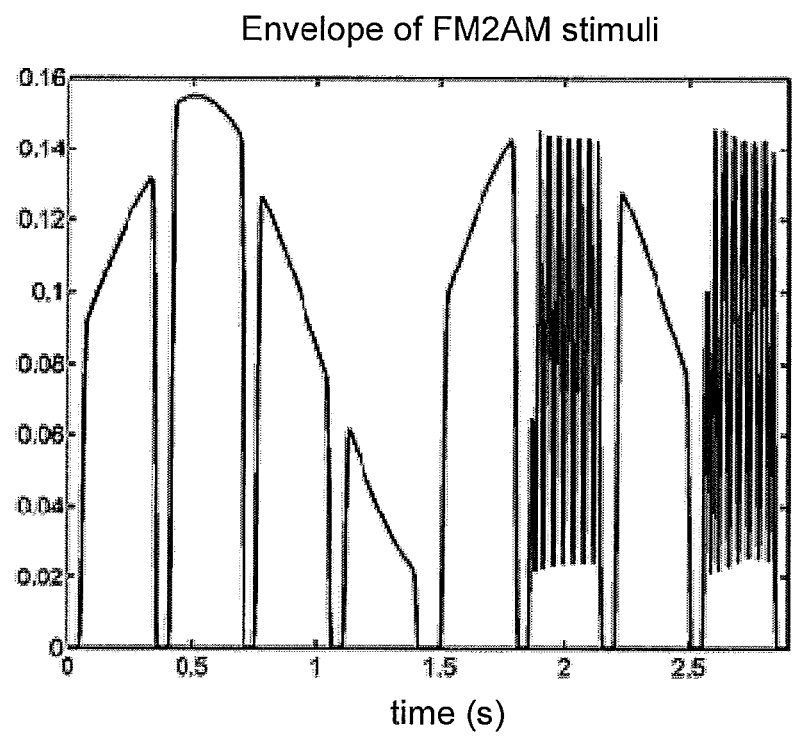
FIG. 16 shows the FM function applied as different AM rates [0-0.16] (strength or amplitude) vs. time [0-3 s] using the FM2AM scheme of the present disclosure.

In FIG. 16 the FM function is applied as an increase in the amplitude modulation rate, specifically $$FM2AM(t) = B + D\sin\left(2\pi\left(\frac{f_0}{CS} + \frac{f_\Delta}{SS}\right)\right),$$

where CS is the carrier scaling and SS is the shift scaling, such that the applied modulation rate is a linear combination of the carrier and shift frequencies. Since $f_0 \gg f_\Delta$, $f_0 \gg f_\Delta$ it seems appropriate that CS≫ SS CS≫SS as well. This also includes CS=∞ such that only the shift frequency is coded in amplitude modulation rate.

Figure 17:
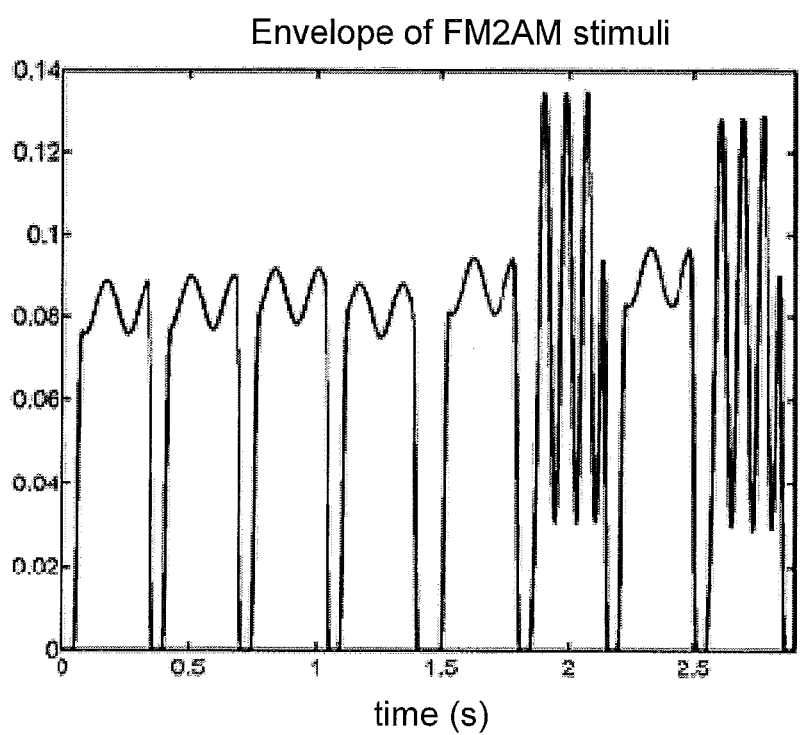
FIG. 17 shows the FM function applied as different AM rates and AM modulation depths [0-0.14] (strength or amplitude) vs. time [0-3 s] using the FM2AM scheme of the present disclosure.

In FIG. 17 the FM function is applied as an increase in the amplitude modulation rate as well as the amplitude modulation depth, specifically $$R = R_{max}\left(\frac{1}{2} + \frac{f_\Delta}{f_0}\right)$$

$$D = D_{max}\left(1 - \frac{3f_\Delta}{2f_0}\right)$$

$$FM2AM(t) = B + D\sin(2\pi t R t)$$

Figure 18:
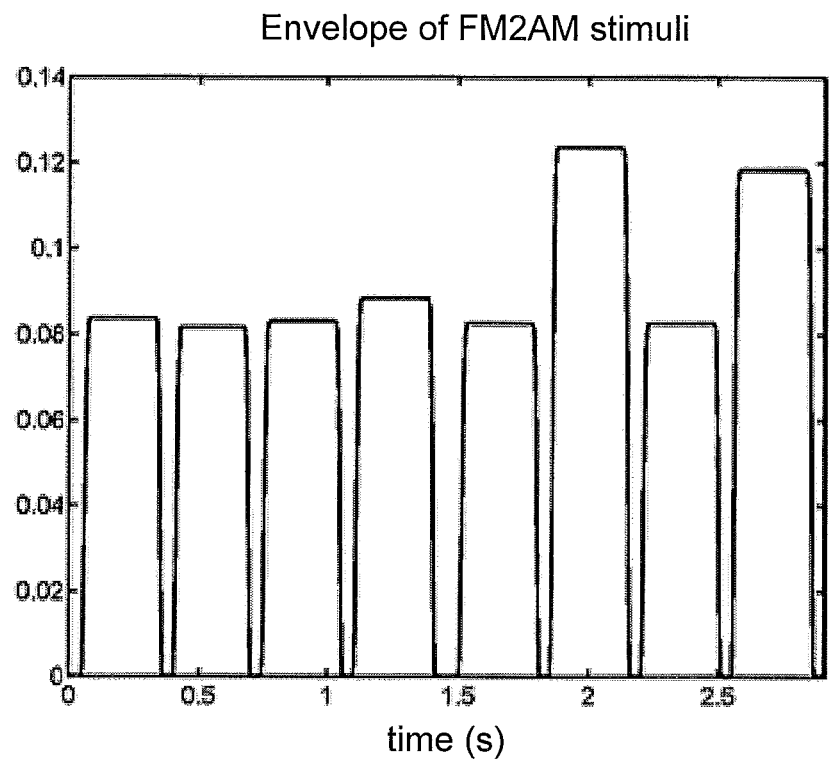
FIG. 18 shows the FM function applied as level changes [0-0.14] (strength or amplitude) vs. time [0-3 s] using the FM2AM scheme of the present disclosure.

In FIG. 18 the FM function is applied as an increase in the amplitude of the stimuli, specifically $$FM2AM(t) = SomeAuditoryFilterTemplate\left(abs(scl)\frac{f_\Delta g(t)}{f_{centre}}, 30\right)$$

where $g(t)=1^{g(t)=1}$ when the stimuli are shifted and zero when it is harmonic. Moreover, if scl $^{scl}$ is negative, then the frequency shift is converted to an amplification by using min $(FM2AM(t), gain_{max})^{min\ (FM2AM(t),\ gain_{max})}$. This ensures that the level is not increased too much.

Figure 19:
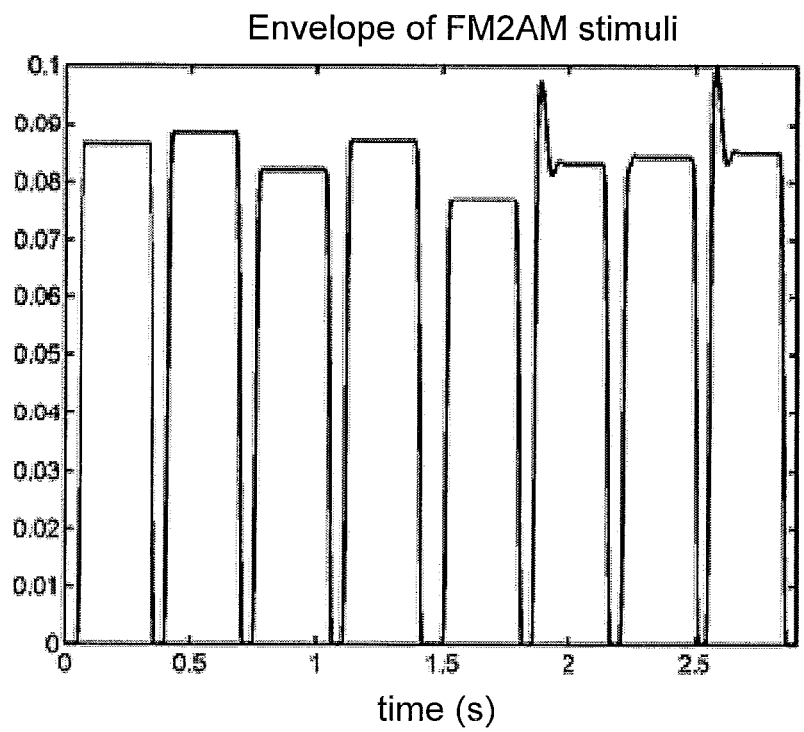
FIG. 19 shows changes in FM function applied as decayed level change [0-0.1] vs. time [0-3 s] using the FM2AM scheme of the present disclosure.

In FIG. 19 the changes to the FM function are applied as sudden increases and decays of the stimuli amplitude. Specifically the FM2AM(t) from FIG. 18 is gated by a independent FM rate change detector in order to obtain the decay.

All examples share that the FM2AM applies the FM function in a manner such that it can also be perceived even if only temporal envelopes are preserved by the hearing impaired.

Particular embodiments of the invention include:

a. that the original band signal and the new band limited signal according to the invention are combined with weights so they can be combined differently depending on the SNR.

b. that the weight of the original signal is zero for negative SNRs (passing only the "FM" information).

c. SNR in a given band may determine which band to copy to and from.

Preferably FM demodulation techniques from the telecommunication field can be utilized. For example phase-locked loops (PLLs) have good noise resistance properties, and includes differently designable parameters for capture region (the region where which the strongest FM-signal is given priority) and lock-in region (the frequency range where FM signals are decoded). The PLLs shall be designed so they can capture and lock in the variations in the fundamental frequency $F_0$ (and harmonics) of typical voices.

At least one PLL per filterbank band spanning the speech region is required. The PLL will then lock on to the strongest carrier within that band. Preferably the filterbank shall be (highly) overlapping to allow voices with nearby $F_0$ to be locked on to.

An alternative for FM demodulation is the Teager operator (Kaiser, 1990), which is relatively simple to implement, but has not-so-good noise resistance properties.

Figure 1A:
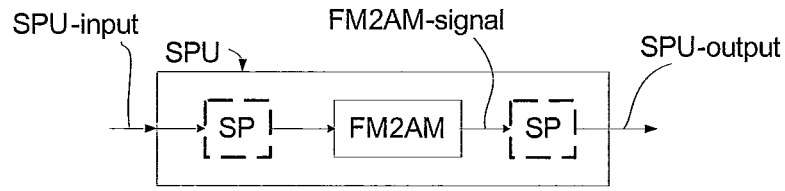
FIG. 1 shows a signal processing device according to an embodiment of the invention (FIG. 1a), a listening device comprising a signal processing device (FIG. 1b), a first audio processing system comprising a signal processing device and a PC (FIG. c) and a second audio processing system comprising a signal processing device and a TV-set (FIG. 1d)
Figure 1B:
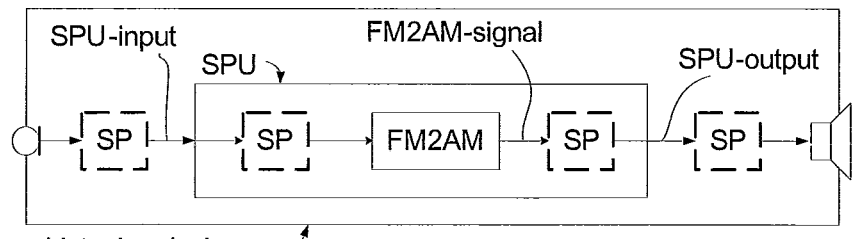
Figure 1C:
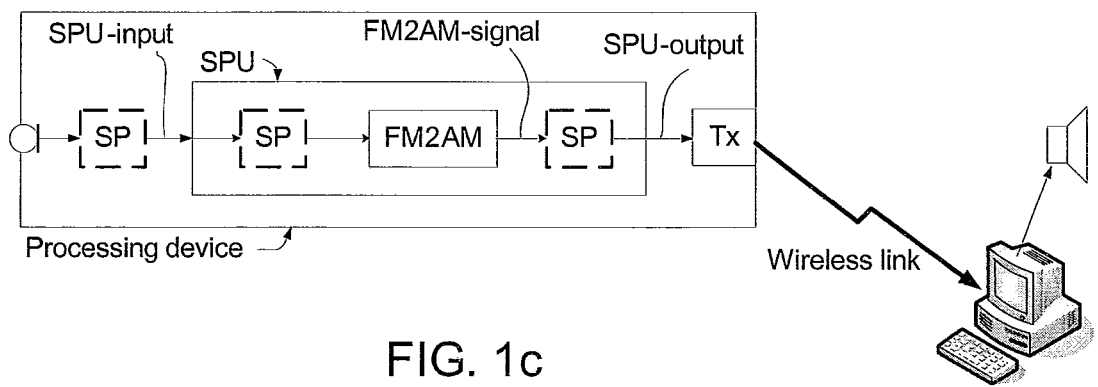
Figure 1D:
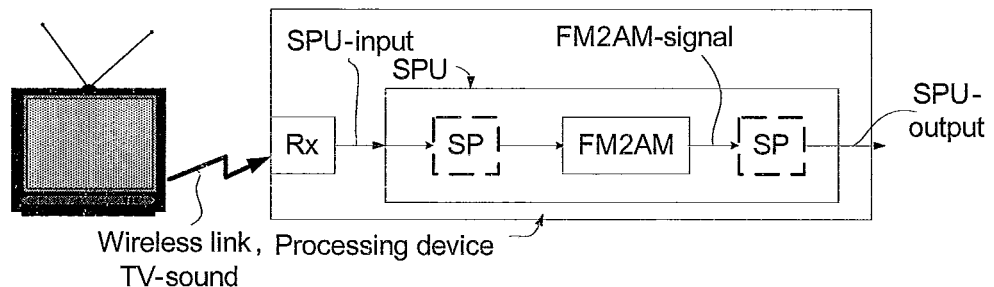

FIG. 1 shows a signal processing device according to an embodiment of the invention (FIG. 1a), a listening device comprising a signal processing device (FIG. 1b), a first audio processing system comprising a signal processing device and a PC (FIG. 1c) and a second audio processing system comprising a signal processing device and a TV-set (FIG. 1d).

FIG. 1a shows an embodiment of a signal processing device (SPU) according to the invention. The signal processing device (SPU) receives an SPU-input signal e.g. comprising frequencies in a range between a minimum frequency and a maximum frequency, and provides a processed SPU output signal. The signal processing device further comprises an FM to AM transformation unit (FM2AM) for transforming at least one signal originating from the SPU-input signal and comprising at least a part of the frequency range of the SPU-input signal from a frequency modulated signal to an amplitude modulated signal providing an FM2AM signal. SP denotes optional signal processing blocks in the signal path between input and output of the signal processing device. The signal processing device is preferably adapted to a particular user's hearing impairment by converting a frequency modulated input signal to an amplitude modulated output signal at least in one frequency range of the input signal. In an embodiment, the processed SPU-output signal is used as an input to an ASR (Automatic Speech Recognition) system, such system being sensitive to the AM and FM information in its input signal in ways that resemble that of some hearing impaired persons.

FIG. 1b shows a listening device, e.g. a hearing instrument, comprising an input transducer (here a microphone) for converting an input sound to an electrical input signal, a signal processing device (SPU) as shown in FIG. 1a for processing an SPU-input signal originating from the electrical input signal and comprising frequencies in a range between a minimum frequency and a maximum frequency, and providing a processed SPU output signal, and an output transducer (here a receiver) for generating an output stimulus representative of the input sound to a user based on a signal originating from the SPU-output signal. SP denotes optional signal processing blocks in the signal path between input and output transducer. In FIG. 1b, the optional SP-units are located outside as well as inside the SPU-unit to indicate that (other) signal processing can be performed before as well as after the FM2AM transformation unit.

FIG. 1c shows an audio processing system comprising a signal processing device (e.g. as shown in FIG. 1a) receiving its input from a microphone (thereby e.g. implementing a customized wireless microphone) and a PC comprising a loudspeaker with a wireless link between the signal processing device and the PC (the wireless link comprising a transmitter (Tx) (and optionally a receiver for 2-way communication) in the SPU and a corresponding receiver (and optionally a transmitter) in the PC). Alternatively, the signal processing device and, optionally, the microphone may form part of the PC, thereby making the wireless link between them superfluous. Such a system may be advantageous to implement a customized audio interface in the PC, the input to the customized signal processing unit being e.g. a spoken input picked up by the microphone (as shown in FIG. 1c) or, alternatively, an electronic signal representing e.g. speech, such as an IP-based telephone conversation received via a network (e.g. the Internet) or an audio signal streamed from an audio source in the environment, e.g. a TV (see also FIG. 1d). Alternatively, the audio processing system may form part of (or be used as a pre-processing system) for an ASR system (e.g. implemented on the PC to convert speech to text on the PC), the processed SPU-output signal being used as an input to the ASR algorithms.

FIG. 1d shows an audio processing system comprising a TV-set and processing device comprising a signal processing device (e.g. as shown in FIG. 1a) with a wireless link between them, the TV-set comprising a wireless transmitter and the processing device comprising a corresponding wireless receiver (Rx). The wireless link is e.g. one way, but may alternatively be two way (e.g. to ensure a proper frequency channel). The TV-set transmits an audio signal to the processing device where it is received and processed in the SPU (customized to a particular user) to provide an improved output. The improved output (SPU-output) may be connected to a loud speaker (receiver) to provide an output sound which is better perceived by the user. Alternatively, the SPU-output may be forwarded either directly to a listening device (if the processing device form part of the listening device) or be wirelessly transmitted to a listening device, such as a hearing instrument (if the processing device form part of an intermediate device between the TV-set and a listening device, such intermediate device being e.g. an audio selection device). The wireless link may e.g. be based on inductive (near-field) communication or, alternatively, on radiated fields. Alternatively, the connection between the TV-set and the processing device may be a wired connection, e.g. a cable, or the processing device may form part of the TV-set or a set-top box connected to the TV.

Figure 2:
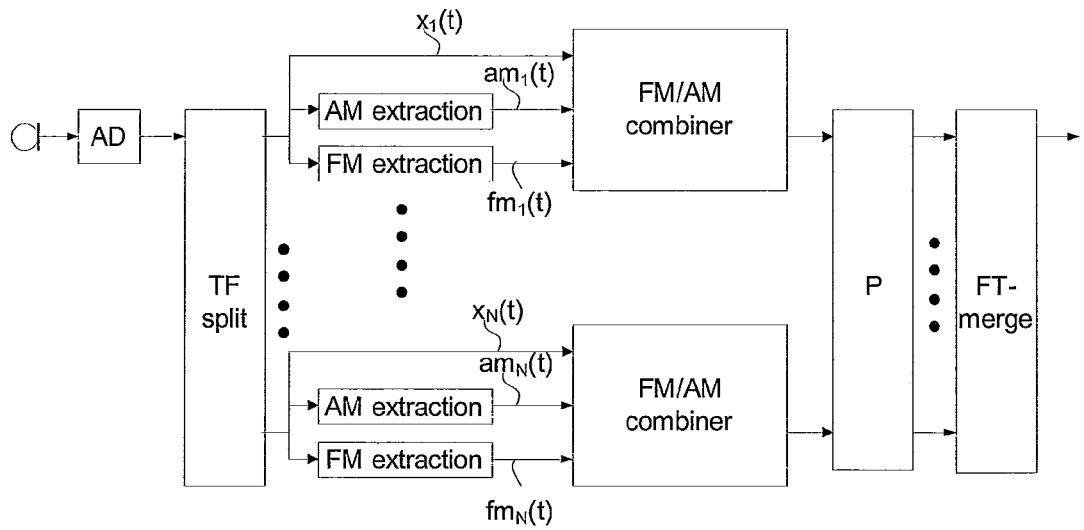
FIG. 2 shows parts of a listening device comprising a signal processing device according to an embodiment of the invention.

FIG. 2 shows parts of a listening device comprising a signal processing device according to an embodiment of the invention.

Figure 3:
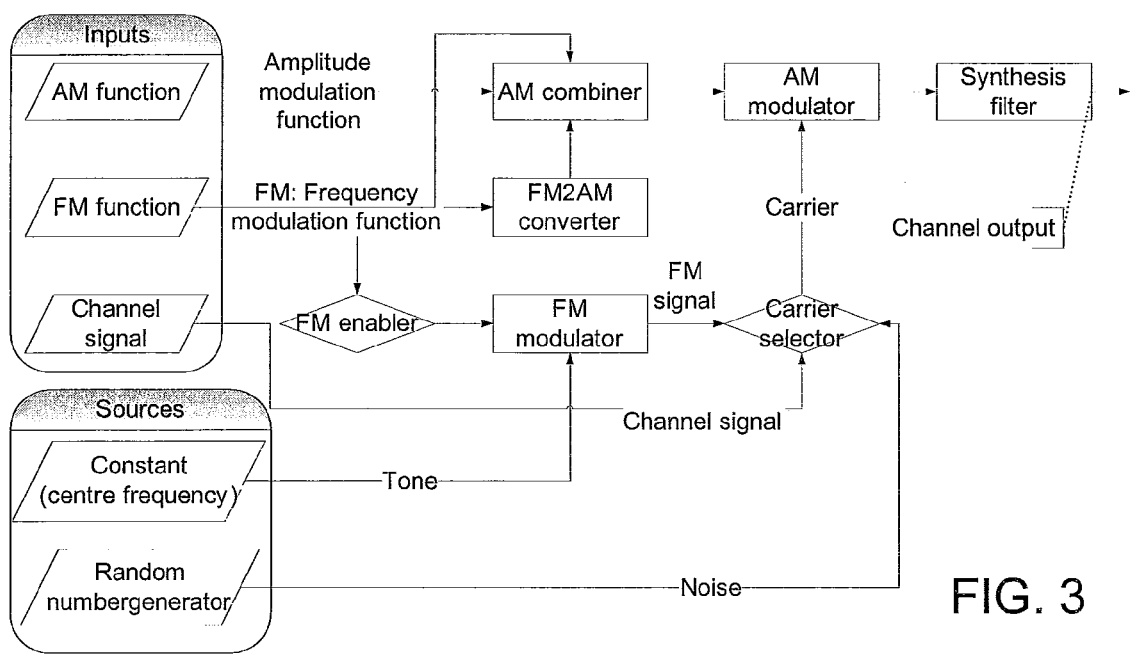
FIG. 3 shows an FM/AM combiner part of a signal processing device according to an embodiment of the invention.

FIG. 2 shows parts of a listening device comprising a microphone for converting an input sound to an analogue electrical input signal, an analogue to digital converter (AD) for converting the analogue electrical input signal to a digital electrical input signal (by sampling the electrical input signal with a predefined sampling frequency $f_s$ to provide a digitized input signal comprising digital time samples $y_m$), which is fed to a signal processing device. The signal processing device comprises in the present embodiment a time to time-frequency transformation unit (TF-split, wherein time frames of the input signal, each comprising a number M of digital time samples $y_m$ (n=1, 2, . . . M), corresponding to a frame length in time of $L=M/f_s$, are subject to a time to frequency transformation to provide corresponding spectra of frequency samples). The TF-split unit splits the input signal into a number of frequency bands N, each signal $x_n$ of a band being a time varying signal containing frequencies of that band (n=1, 2, . . . , N). The signal path of each band is split in three paths comprising the input signal $x_n$, an AM extraction unit and an FM extraction unit, respectively. The AM extraction unit of a given band n extracts the amplitude modulation function (envelope) $am_n(t)$ of the signal $x_n$ of that band (t being time). The FM extraction unit of a given band n extracts the frequency modulation function $fm_n(t)$ of the signal $x_n$ of that band. The input signal $x_n$ and the outputs of the AM extraction and FM extraction units, respectively, are fed to a combiner unit (FM/AM combiner). An embodiment of the combiner unit is shown in FIG. 3. The FM/AM combiner combines the channel signal, AM function and FM function as well as an AM function extracted from the FM function according to the current sound environment and user preferences. An example of the AM and FM extraction would be the Hilbert envelope and the time derivative of the instantaneous phase (cf. e.g. Proakis and Manolakis (1996). Moreover, Teagers Energy Operator can be used to extract the AM and FM as shown by Kaiser (1990), Maragos et. al. (1993a), or Zhou et al. (2001). Similarly, the AM and FM can be extracted using Taylor approximations as recently suggested by Betser et al. (2008). The output signal of the FM/AM combiner unit of a given band is fed to a processing unit for optional further processing (block P in FIG. 2, e.g. for adaptation to a user's particular needs for frequency dependent gain, compression, etc.). The signal processing device further comprises an FT-merge unit that merges the individual band signals to an SPU-output signal in the time domain. The listening device may further comprise a transducer (not shown, but cf. e.g. FIG. 1b) for generating an output stimulus representative of the input sound to a user based on a signal originating from the signal processing unit. The output of the signal processing device (cf. e.g. SPU-output in FIG. 1) can e.g. be fed to a receiver (e.g. of a hearing instrument) for presenting an improved sound signal to a hearing impaired user.

The hearing device may of course further comprise other functional units, e.g. feedback cancellation units, etc.

FIG. 3 shows an FM/AM combiner part of a signal processing device according to an embodiment of the invention. The purpose of the block is to create a Channel output signal by non-linear combinations of the AM function, FM function, Channel signal, centre frequency and noise. This is achieved by imposing an amplitude modulation (constructed from the AM and FM functions) on a carrier (being a pure tone, a frequency modulated pure tone (using the FM function), the channel signal itself, or random noise).

Assume for now that the amplitude modulation and frequency modulation in the channel signal is estimated and applied as the AM and FM function. Here the AM function describes the envelope in the channel signal and the FM function describes the instantaneous frequency of the channel signal. The direct connection between the FM function and the AM combiner allows the information in the FM function to be provided directly as a level cue; e.g. where higher frequency yields louder channel output. The connection from the FM function through the FM2AM converter to the AM combiner allows the information in the FM function to be processed—e.g. resembling FM2AM conversion in a normal ear—before it is applied as amplitude modulation.

Until now, only the left hand side input to the AM modulator has been described. The bottom input to the AM modulator—labelled Carrier—has four modes.

| Mode | Carrier selector | Channel output |
|---|---|---|
| 1 | FM function + constant giving a FM signal | A frequency modulated signal amplitude modulated by the AM combiner output |
| 2 | Constant giving a pure tone | A pure tone amplitude modulated by the AM combiner output |

| Mode | Carrier selector | Channel output |
|---|---|---|
| 3 | Noise | A noise like signal amplitude modulated by the AM combiner output. |
| 4 | Channel signal | The channel signal with additional amplitude modulation from the AM combiner output |

Mode #4 is different to the other modes since the carrier signal might already be amplitude modulated. The FM signal and pure tone have constant level, whilst the noise signal has a constant average level. Finally the Synthesis filter restricts the bandwidth of the output signal, as both amplitude and frequency modulation results in energy at frequencies not present in the input signals.

The FM/AM combiner has now been described for the setup where the AM and FM functions were extracted from the Channel signal itself. Nevertheless can the Channel signal, AM function, and/or FM function be connected to similar outputs from other frequency regions. Likewise can the Channel signal, AM function, and/or FM function be connected to enhanced (e.g. similarly to noise reduction) representations of that information.

The two main steps in the processing in FIG. 3 are the AM combiner and the FM2AM converter. The AM combiner can select or combine from three sources of amplitude modulation, the provided AM function, the provided FM function or the FM-to-AM converted function. The AM combiner can select the AM function in situations with high SNR (where the AM function is believed to be good enough). In situations where the SNR is lower it can combine the AM and FM functions. And if the SNR is even worse it can select the FM function and discard the AM function completely. Finally the FM function can also be so distorted that it cannot be used, and there the channel signal or silence remains as options. This behaviour is outlined in FIG. 7.

The processing allows the FM function to be utilized in three ways (possibly all together at one time). The FM function can be applied to the channel signal (e.g. the SPU-input signal of the frequency range in question) (or its envelope) via the AM combiner, the FM function can be converted into an AM function using the FM2AM converter and AM combiner, and/or the FM function can generate an FM signal using the FM modulator. An example of the operation of the AM combiner is given in FIG. 7, that sketches a linear combination of the AM function and the AM function extracted using the FM2AM converter as a function of the local (in time and frequency) signal to noise ratio (SNR). The AM/FM combiner can be parameterized (essentially by omitting the connections between FM function and AM combiner) to yield the same processing as in the FAME processing suggested by Zeng et al. (2005). If the AM function is extracted from the channel signal as specified in Zeng et al. (2005), and the FM function also as specified in Zeng et al. (2005), and the AM combiner only uses the AM function and not the FM function or the output from the FM2AM converter, and the FM signal is selected as carrier with the FM function input enabled, then the processing shown in FIG. 3 resembles the FAME processing due to Zeng et al. (2005). If it is beneficial to the user, the FM can be enhanced prior to the FM/AM combiner (FIG. 3. is the FM/AM combiner) such that a cleaner FM function can be used in the signal modification via the AM and FM modulators.

Figure 11A:
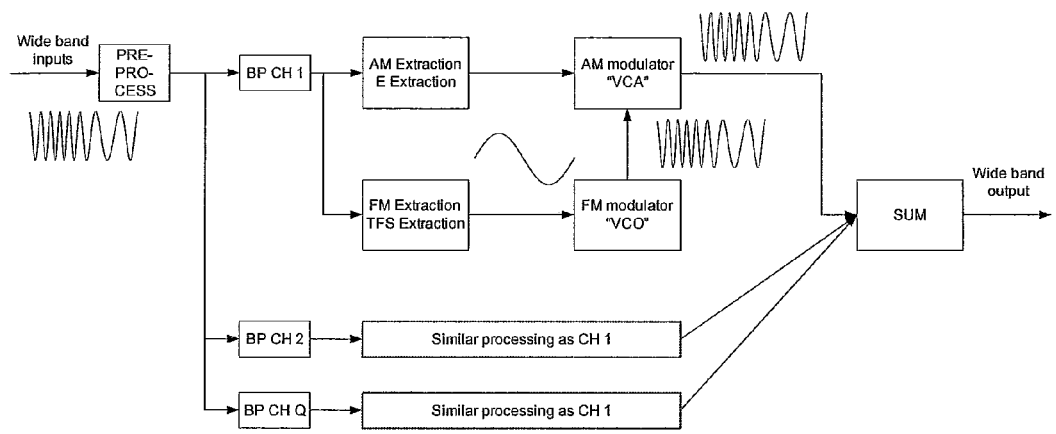
FIG. 11 illustrates the difference between how the channel processing circuitry of two processing schemes treat a specific input signal, FIG. 11a showing the effect of prior art FAME principle (Zeng et al. (2005)) and FIG. 11b showing the effect of the principle of the present disclosure.
Figure 11B:
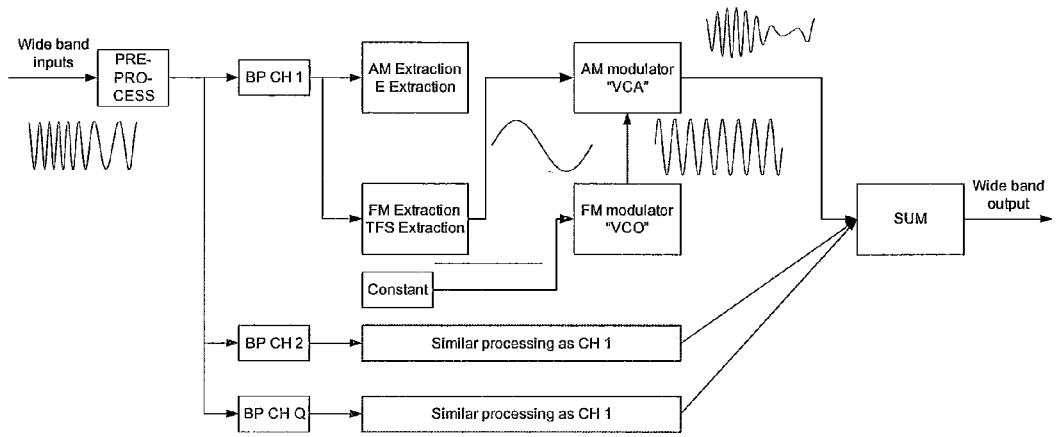

To further elucidate the difference between the FAME processing of Zeng et al. (2005) and the scheme according to the present disclosure, the two principles are schematically illustrated in FIG. 11. The different characteristics of the AM and FM modulators of the upper and lower branches, respectively, of the channel-processing of the bandpass filtered input signal are easily identified in FIGS. 11a and 11b and illustrated by the schematic waveforms associated with selected signals of the circuits. The AM modulator applies a time-varying amplitude controlled by the left input to the bottom input to the block. The term Voltage Controlled Amplifier (VCA), originating from analog electronics, describes the functionality. The FM modulator applies a time-varying change of the instantaneous frequency of the bottom input, controlled by the left input to the block. If the bottom input is omitted it can be assumed to be one. In that case the term Voltage Controlled Oscillator (VCO), originating from analog electronics, describes the functionality.

FIG. 11 illustrates the difference between the two schemes by looking at how the channel processing circuitry of the FAME principle (FIG. 11a) and the present disclosure (FIG. 11b) modifies a specific input signal, here selected to be a frequency-modulated tone (in short the FM signal). For simplicity it is assumed in FIG. 11 that the FM signal fits channel 1 (CH 1) and is processed in that channel only.

FIG. 11a shows how the frequency-modulated tone is passed through the FAME processing blocks. The characteristics of the input signal are preserved, since the instantaneous frequency is changing and the temporal envelope is flat.

FIG. 11b shows how the frequency-modulated tone is passed through the FM2AM processing blocks as proposed by the present inventors. The FM2AM processing blocks processes the FM signal in a different manner than the FAME processing blocks. The amplitude-modulation function and frequency-modulation function are extracted in similar manners. The frequency-modulation function is, however, passed as the gain-controlling input to the AM modulator that adjusts the temporal envelope of the pure tone output from the FM modulator.

The frequency modulation function FM or the transformed frequency modulation function FM2AM output is used to amplitude modulate a constant envelope input signal to provide a resulting amplitude modulated signal. Moreover, the FM or FM2AM can by used to amplitude modulate a signal already containing amplitude modulation in order to enhance the already present or add more amplitude modulations.

The AM combiner can combine and select between the three modulation sources, the (input) Amplitude Modulation function, the (raw) Frequency modulation function and the Amplitude Modulation function extracted from the Frequency Modulation function (FM2AM output signal).

The Carrier selector selects between the channel signal (SPU-input signal of the frequency range in question), the FM modulated signal, or the noise carrier The FM enabler controls whether the FM function is allowed to modulate the pure tone at the centre frequency.

Figure 4:
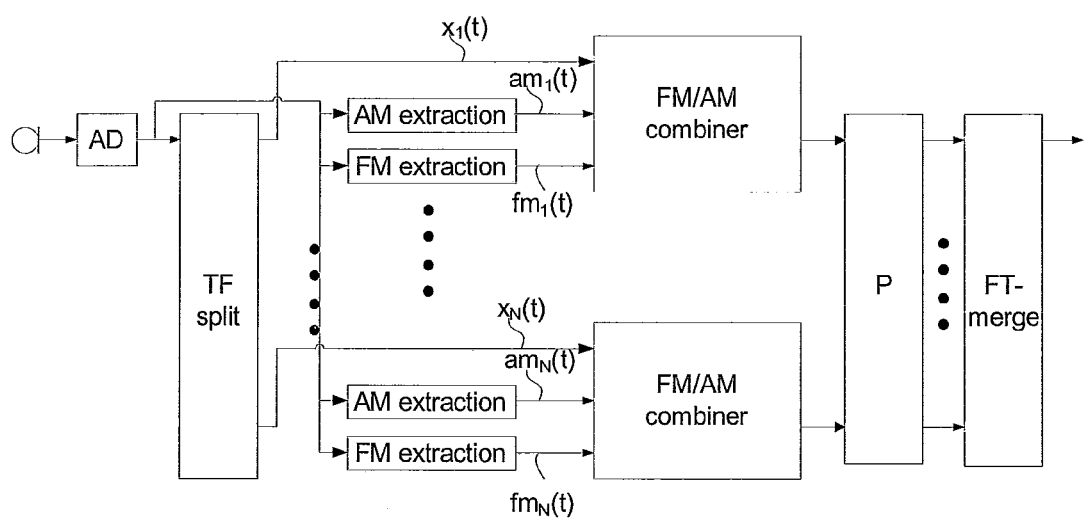
FIG. 4 shows parts of a listening device comprising a signal processing device according to an embodiment of the invention.

FIG. 4 shows parts of a listening device comprising a signal processing device according to an embodiment of the invention. The embodiment of FIG. 4 is identical to that of FIG. 2 except that the input to the AM- and FM-demodulation units (AM extraction and FM extraction, respectively, in FIGS. 2 and 4) is the digital electrical input signal (here taken directly from the analog to digital (AD) converter, which is the input to the signal processing device comprising the full frequency range (full bandwidth). In the embodiment in FIG. 2, the input to the AM- and FM-demodulation units are taken from the filter bank or time frequency splitting unit (TF split in FIGS. 2 and 4) and contain only their respective (possibly overlapping) frequency bands.

Figure 5A:
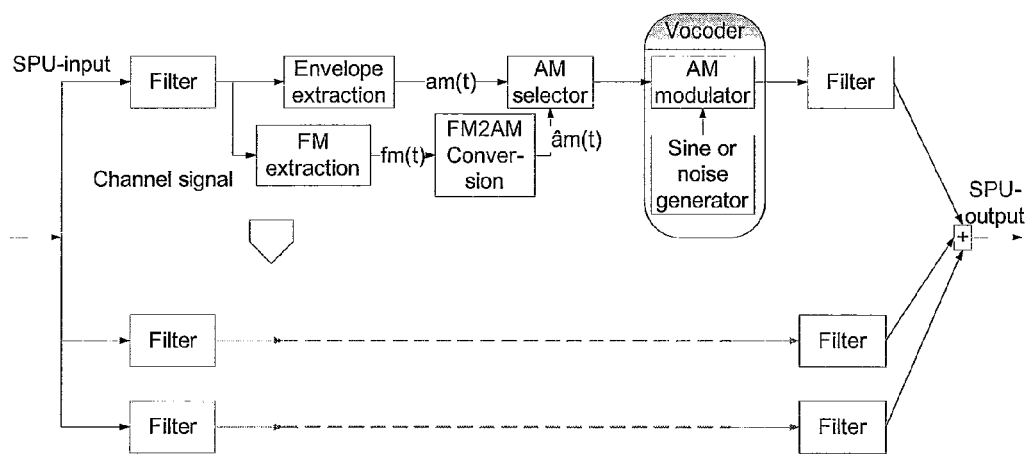
FIG. 5 shows parts of a signal processing device according to an embodiment of the invention, FIG. 5a comprising a filter bank and separate AM and FM demodulation units, FIG. 5b comprising phase locked loop-based extraction of the AM- and FM-functions.
Figure 5B:
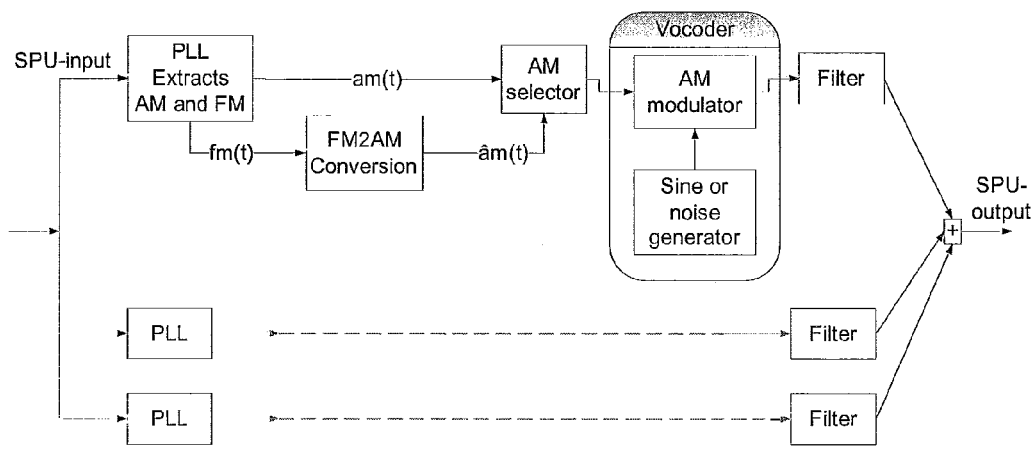

FIG. 4 suggests an alternative configuration of the signal processing where the frequency selectivity is included in the AM and FM extraction, e.g. using Phase-Locked Loops (PLL) as illustrated in more detail in FIG. 5b. If the individual channel signals are not necessary in the processing, the TF split can be omitted completely, if that is not the case connection the direct AM and FM extraction allow for shorter estimation delays in those blocks. Moreover, as a hybrid between the embodiments of FIG. 4 and FIG. 2, only the FM extraction could be connected to the full bandwidth signal whilst connecting the AM extraction units to the individual (band limited) channel signals.

An example of a combined AM and FM extraction using Phase-Locked Loops is given by Wang and Kumaresan (2006) (cf. FIG. 2 therein). However, their processing requires a band pass filter in front of the AM-FM extraction.

FIG. 5 shows parts of a signal processing device according to an embodiment of the invention, FIG. 5a comprising a filter bank and separate AM and FM demodulation units, FIG. 5b comprising phase locked loop-based extraction of the AM- and FM-functions.

The embodiments of a signal processing device in FIGS. 5a and 5b both comprise—in each frequency range or band—an AM selector, which as inputs have the amplitude modulation function am(t) for that frequency range and the output âm(t) of an FM2AM Conversion unit, whose input is the frequency modulation function fm(t) and whose output comprises the FM-information converted to an amplitude modulation function âm(t) for that frequency range. The output of the AM selector, a weighted amplitude modulation signal, comprising a weighted combination of the inputs am(t) and âm(t) for a particular frequency range is fed to a Vocoder unit comprising an AM modulator unit and a frequency generator unit wherein a sinusoidal of a particular frequency (e.g. the mid frequency of the frequency range in question) or a noise can be generated and amplitude modulated by the weighted amplitude modulation signal. The output of the Vocoder for a particular frequency range is an amplitude modulated weighted signal that is fed to a Filter for limiting the output signal to the frequency range in question and optionally for ensuring an appropriate frequency overlap with neighboring frequency ranges. The out of the Filter is added with those of the other frequency ranges to form the SPU-output signal. This signal can form the basis for generating an improved output stimulus to a hearing impaired user who cannot by himself access the FM modulation signal and subsequently transform it into an AM modulation signal. Optionally the FM signal can by reproduced in the sine-generator using the FM modulation signal.

The differences between the embodiments of FIGS. 5a and 5b lie on the input side of the signal processing device. The input signal (SPU-input in FIG. 5) of the signal processing device, here assumed to be an electrical signal in the time domain, is in FIG. 5a fed to a filter bank (represented by Filter units in FIG. 5a, one for each frequency range) for splitting the input signal into a number of—possibly overlapping—frequency ranges. In FIG. 5b the input signal is fed to a number of phase locked loop units (PLL units in FIG. 5b), one for each frequency range into which the input signal is to be separately processed. In the embodiment of FIG. 5a, the output of a Filter of the filter bank for a particular frequency range is fed to an AM demodulation unit (here based on Envelope extraction) extracting the amplitude modulation function am(t) (fed to the AM selector) as well as to an FM extraction unit providing the frequency modulation function fm(t) (fed to the FM2AM Conversion unit) for that frequency range. In the embodiment of FIG. 5b, the PLL-unit of a particular frequency range extracts the amplitude modulation function am(t) (fed to the AM selector) as well as the frequency modulation function fm(t) (fed to the FM2AM Conversion unit) for that frequency range.

Figure 6:
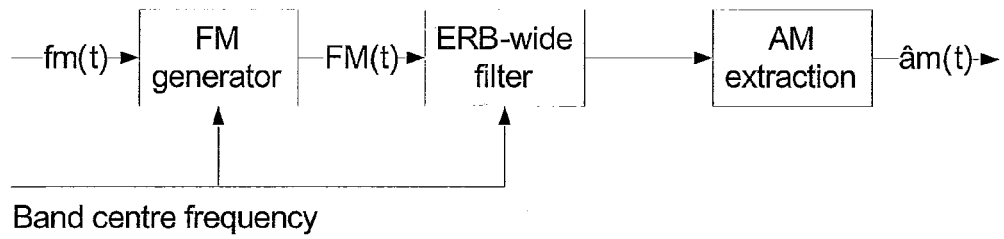
FIG. 6 shows an FM2AM converter unit according to an embodiment of the invention, FIG. 7 schematically illustrates a scheme for determining the weighting functions of a weighting unit according to an embodiment of the invention.

FIG. 6 shows an FM2AM converter unit according to an embodiment of the invention. FIG. 6 outlines a simple way of converting the FM function into an AM function, mimicking an FM2AM conversion that the normal cochlea, as suggested by Ghitza (2001), is believed to provide. The reduced frequently selectivity of the damaged cochlea (i.e. wider auditory filters) reduced the amount of FM2AM conversion and thus limits this process. The FM generator modulates a sinusoid at band centre frequency with a modulation input $fm_n(t)$. The output of the FM generator $FM_n(t)$ is a pure FM signal with a flat envelope, which is fed to an ERB-wide filter centered at bank centre frequency. The output of the ERB-wide filter is fed to an AM extraction unit, which provides the output FM2AM signal $\hat{a}m_n(t)$, i.e. an AM signal based on the FM2AM that the hearing impairment disables.

Figure 7:
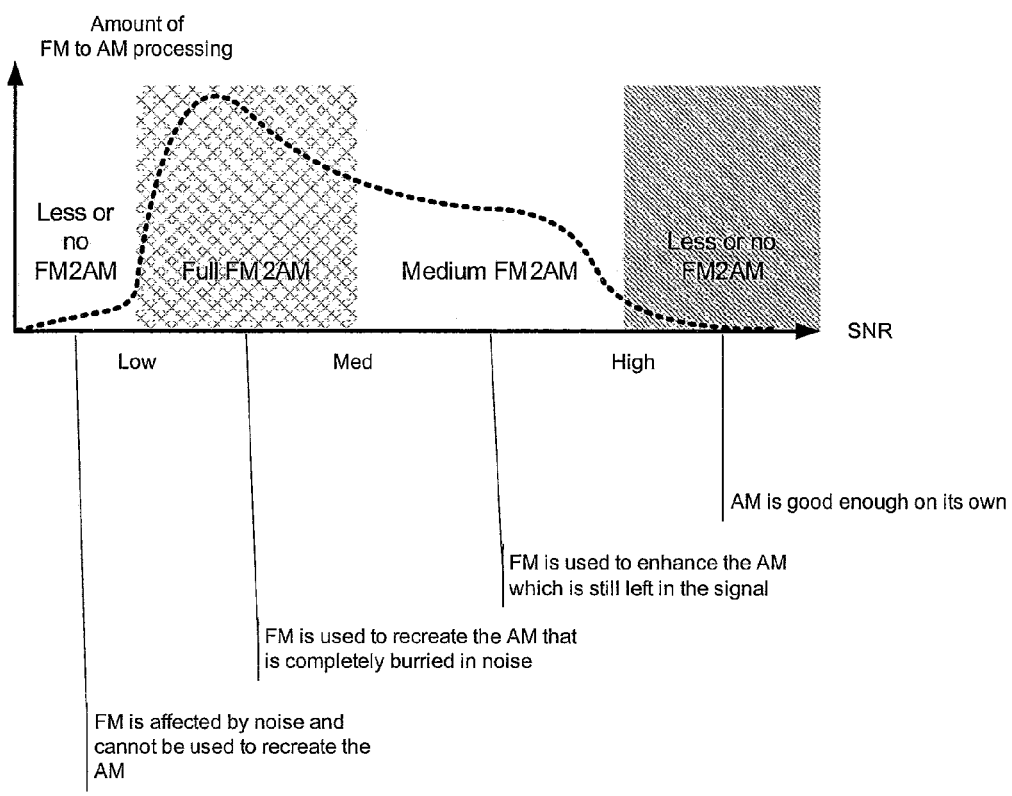

FIG. 7 illustrates a scheme for determining the weighting functions of a weighting unit according to an embodiment of the invention. FIG. 7 sketches the influence of the local SNR (in time and frequency) on the weighting of the AM function extracted from the FM function (the FM2AM-signal) compared to the AM function that the input provides. The sketch suggests 4 main regions of operation, two where there is very little or no FM2AM processing either due to the lack of reliable estimation of the FM function, i.e. at very low (or even negative) local SNR, or at very high local SNR where the processing is not necessary. As the local SNR is decreased from the high SNR case the need for FM2AM processing increases and at some point the provided amplitude modulation could be solely based on the FM function.

From FIG. 7 the following simplified scheme for applying weighting factors can be derived, where $k_{am}$ is the weighting factor on the amplitude modulation function am(t) (e.g. individualized to different frequency ranges or bands, n, n=1, 2, . . . , N) and $k_{fm}$ is the weighting factor on the frequency modulation function fm(t) (e.g. individualized to different frequency ranges or bands, n, n=1, 2, . . . , N) or the AM2FM-signal am2fm(t) or âm(t) (e.g. individualized to different frequency ranges or bands, n, n=1, 2, . . . , N). The scheme can e.g. be applied in the AM combiner of FIG. 3 (assuming that the FM function input is disabled), such as in the AM selector of FIG. 5a or 5b.

Range 1 ($SNR \geq SNR_{high}$): AM is good enough on its own=>$k_{am}$=1, $k_{fm}$=0.

Range 2 ($SNR_{high}$>$SNR \geq SNR_{med}$): FM is used to enhance the AM which is still left in the signal=>$k_{am}$=½, $k_{fm}$=½.

Range 3 ($SNR_{med}$>$SNR \geq SNR_{low}$): FM is used to recreate the AM that is completely buried in noise=>$k_{am}$=0, $k_{fm}$=1.

Range 4 ($SNR_{low}$>SNR): FM is affected by noise and cannot be used to recreate the AM=>$k_{fm}$=0.

Figure 8:
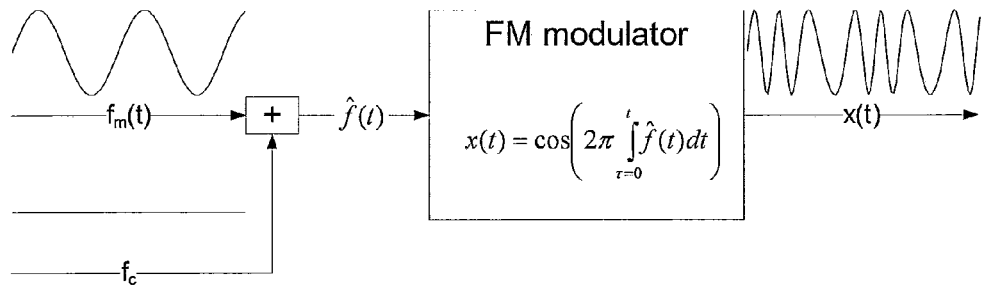
FIG. 8 shows an embodiment of an FM modulator for use in a signal processing device according to an embodiment of the present invention.

FIG. 8 shows an embodiment of an FM modulator for use in a signal processing device according to an embodiment of the present invention.

The input signal to the FM modulator is a sum of the FM function fm(t) and a channel centre frequency fc ($fc_N$).

In one embodiment, the FM modulator is basically a cosine and an integrator. Its output is given by the following equation $$x(t) = \cos\left(2\pi \int_{\tau=0}^{t} \hat{f}(\tau) d\tau\right) = \cos\left(2\pi fc_N t + \int_{\tau=0}^{t} fm_N(\tau) d\tau\right),$$

where $fc_N$ is the centre frequency of the band in question and fm(t) is the FM function. The output x(t) of the FM Modulator is a "cosine" where the instantaneous frequency is modulated by fm(t).

Figure 9:
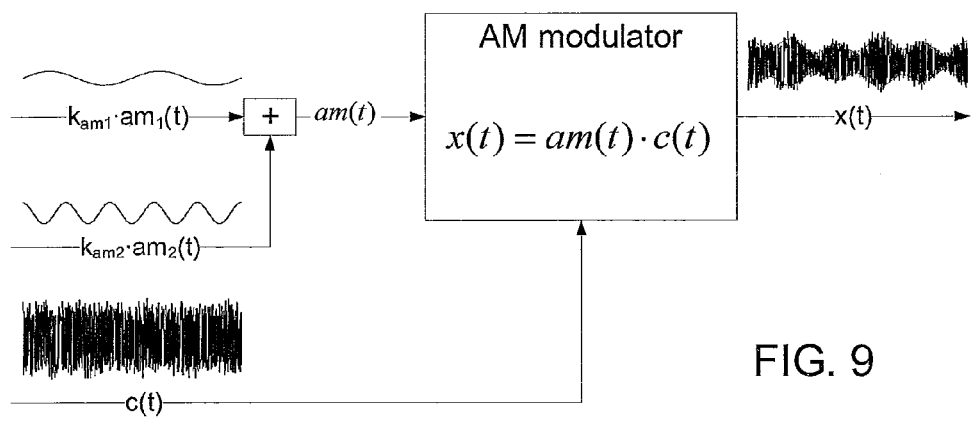
FIG. 9 shows an embodiment of an AM modulator for use in a signal processing device according to an embodiment of the present invention.

FIG. 9 shows an embodiment of an AM modulator for use in a signal processing device according to an embodiment of the present invention.

The AM modulator is a generic amplitude modulation box, in its most basic form here it is just a multiplication of the carrier and the modulation function, e.g. x(t)=am(t)·c(t), where am(t) is the modulation function provided by the AM combiner, and c(t) is the carrier provided by the Carrier selector. The figure shows am(t) as a sum of two AM function sources ($k_{am1}$·$am_1$(t) and $k_{am2}$·$am_2$(t), respectively) applied to a noise carrier c(t), and providing an output x(t) in the form of the noise signal with the imposed amplitude modulation.

FIG. 10 shows an embodiment of an FM2AM converter for use in a signal processing device according to an embodiment of the present invention. The FM2AM converter provides as an output an amplitude modulated (AM) signal $âm_n$(t) based on the frequency modulation (FM) function of that band (n) $fm_n$(t) (or alternatively the frequency modulation function $fm_q$(t) from another frequency band or range q).

Figure 10A:
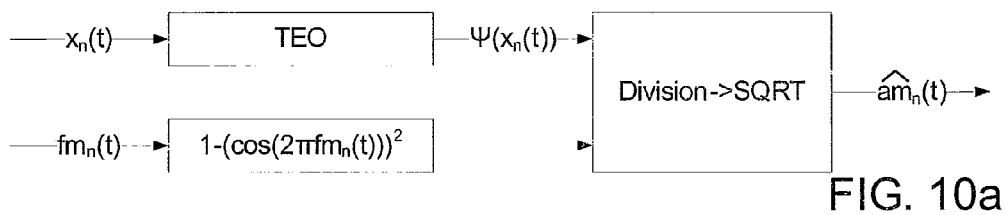
FIG. 10 shows an embodiment of an FM2AM converter for use in a signal processing device according to an embodiment of the present invention.

FIG. 10a show how the AM functions âm(t) can be calculated as a function of the FM function fm(t), by using relations between Teager's Energy Operator and the AM and FM functions using the DESA-1a approximation to Teager's Energy Operator Ψ (Zhou, Hansen, and Kaiser (2001)). (The '^' sign in the AM function 'âm(t)' should ideally have extended over the 'm' in 'am' to follow the notation in (some of) the drawings).

In the embodiment shown in FIG. 10a, the AM function $âm_n$(t) for frequency band n is determined by $$âm_n(t) = \sqrt{\frac{\Psi(x_n(t))}{1 - (\cos(2\pi fm_n(t))^2}}$$

where $x_n$(t) is the channel signal, $fm_n$(t) is the corresponding frequency modulation function, and $\Psi(x_n(t))$ is Teager's Energy Operator acting on the channel signal. The TEO block is Teager's Energy Operator, that calculates $\Psi(x_n(t))$ based on $x_n$(t). The Division→SQRT is a block that calculates the square root of the ratio between the upper and the lower input.

Figure 10B:
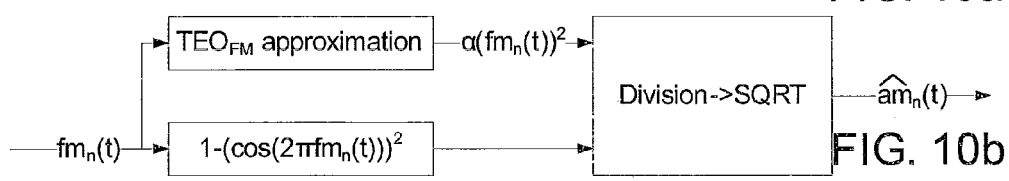

The second embodiment (cf. FIG. 10b) shows an implementation where the channel signal is considered so noisy, such that only the FM part can be relied on in the calculation of Teager's Energy Operator ($TEO_{FM}$ approximation in FIG. 10). Teagers Energy Operator ψ (here $TEO_{FM}$) simplifies in this case to a constant $\alpha^2$ times the square of the FM function ($fm_n$(t))$^2$ (c.f, Kaiser (1990)) for the frequency range or band in question (here denoted n).

$$âm_n(t) = \frac{\alpha fm_n(t)}{\sqrt{1 - (\cos(2\pi fm_n(t))^2}}$$

Other approximations to Teager's Energy Operator (e.g. DESA-1 or DESA-2 in Zhou, Hansen, and Kaiser (2001)) lead to slightly different relations between the AM and FM functions.

The relation between the FM and AM function presented here is a result of knowing that the energy of the channel signal is both a function of the amplitude and instantaneous frequency. Thereby estimating the FM function and calculating the energy of the channel signals provides a link to the AM function. This is quite different to the FM2AM conversion suggested in FIG. 6 that is based on the fact that amplitude of frequency modulated signal passed through a filter depends of the filter shape.

The invention is defined by the features of the independent claim(s). Preferred embodiments are defined in the dependent claims. Any reference numerals in the claims are intended to be non-limiting for their scope.

Some preferred embodiments have been shown in the foregoing, but it should be stressed that the invention is not limited to these, but may be embodied in other ways within the subject-matter defined in the following claims.

REFERENCES

Barney A, Shadle C H, Davies P (1999). Fluid flow in a dynamic mechanical model of the vocal folds and tract. I. Measurements and theory. J. Acoust. Soc. Am., 105(1): 446-455. 1999.

Betser, M., Collen, P., Richard, G. et al. (2008) Estimation of Frequency for AM/FM Models Using the Phase Vocoder Framework. IEEE transactions on Signal Processing 56(2): 505-517. 2008.

Fridberger A, Tomo I, Ulfendahl M, & Boutet de Monvel J (2006). Imaging hair cell transduction at the speed of sound: Dynamic behavior of mammalian stereocilia. PNAS; 103; 1918-1923. 2006

Geisler C D (1991). A realizable cochlear model using feedback from motile outer hair cells. Hear Res 1993 August; 68(2):253-62. 1991

Ghitza O (2001). On the upper cutoff frequency of the auditory critical-band envelope detectors in the context of speech perception. Journal of the Acoustical Society of America, 110(3): pp 1628-1640. 2001

Hopkins K & Moore B C J (2007). Moderate cochlear hearing loss leads to a reduced ability to use temporal fine structure information. J Acoust Soc Am 122(2): 1055-1068. 2007

Hopkins K, Moore B C J, & Stone M A (2008). Effects of moderate cochlear hearing loss on the ability to benefit from temporal fine structure information in speech. J Acoust Soc Am 123(2): 1140-1153. 2008

Hudspeth A J (2005). How the ear's works work: mechano-electrical transduction and amplification by hair cells. C. R. Biologies 328; 155-162. 2005

John M S, Dimitrijevic A, van Roon P, Picton T W (2001). Multiple auditory steady-state responses to AM and FM stimuli. Audiol. Nerurootol. 6(1):12-27. 2001

Kaiser, J. F. On a simple algorithm to calculate the 'energy' of a signal. ICASSP. 1990.

Libermann M C, Gao J, He D Z Z, Wu X, Jia S, & Zuo J (2002). Prestin is required for electromotility of the outer hair cell and for the cochlear amplifier. Nature 419; 300-304. 2002

Liljeryd, L. G., Ekstrand, P., Henn, F., and Kjörling, K. (1998) Source coding enhancement using spectral-band replication. WO 98/57436 (Coding Technologies Sweden AB) 17 Dec. 1998.

Liljeryd, L. G., Ekstrand, P., Henn, F., and Kjörling, K. (2001) Improved spectral translation/folding in the subband domain. WO 01/91111 A1 (CODING TECHNOLOGIES SWEDEN AB) 29 Nov. 2001.

Lorenzi, C., Gilbert, G., Cam, H. et al. (2006) Speech perception problems of the hearing impaired reflect inability to use temporal fine structure. Proceedings of the National Academy of Sciences of the United States of America 103(49):18866-18869. 2006.

Lunner, T. (2007) A system and method for eliminating feedback and noise in a hearing device. WO 2007/006658 (Oticon AS) 18 Jan. 2007.

Maragos, P, Kaiser, J F, and Quatieri, T F (1993a). On Amplitude and Frequency Demodulation Using Energy Operators. IEEE transactions on Signal Processing 41(4):1532-1550. 1993.

Maragos P, Kaiser J F, and Quatieri TF (1993b). Energy Separation in Signal Modulations with Application to Speech Analysis. IEEE Transactions on Signal Processing: 41(10). 1993

McLaughlin S and Maragos P (2006). Nonlinear methods for speech analysis and synthesis. In: Advances in Nonlinear Signal and Image Processing. Eds. Stephen Marshall and Giovanni L. Sicuranza, pp. 103-136, EURASIP Book Series on Signal Processing and Communications, Volume 6. Hindawi Publishing Corporation: New York. 2006

Miller R L, Schilling J R, Franck K R, & Young E (1997). Effects of acoustic trauma on the representation of the vowel /ϵ/ in cat auditory nerve fibers. J Acoust Soc Am 101(6); 3602-3616. 1997

Moore B C & and Skrodzka E (2002). Detection of frequency modulation by hearing-impaired listeners: effects of carrier frequency, modulation rate, and added amplitude modulation. 111(1 Pt 1):327-35. 2002

Picton T W, Dimitrijevic A, and John M S (2002). Multiple auditory steady-state responses. Ann Otol Rhinol Laryngol Suppl. 189:16-21. 2002

Proakis, J. G. and Manolakis (1996), D. G. Digital signal processing: principles, algorithms, and applications Prentice-Hall, Inc. Upper Saddle River, N.J., USA, 1996.

Rabbitt R D, Ayliffe H E, Christensen D, Pamarthy K, Durney C, Clifford S, & Brownell W E (2005). Evidence of Piezoelectric Resonance in Isolated Outer Hair Cells. Biophysical Journal 88; 2257-2265. 2005

Ru P, Chi T, & Shamma S (2003). The synergy between speech production and perception. J Acoust Soc Am 113 (1); 498-515. 2003

Shadle C H, Barney A, and Davies P (1999). Fluid flow in a dynamic mechanical model of the vocal folds and tract. H. Implications for speech production studies. J. Acoust. Soc. Am., 105(1):456-466. 1999

Swaminathan and Heinz (2008). Neural coding of envelope and fine structure in noise degraded speech. Abstract and poster presented at Acoustics 2008 International Conference, Paris, July, 2008.

Teager H M and Teager S M (1990). Evidence for nonlinear sound production mechanisms in the vocal tract. In: Speech Production and Speech Modeling. Eds. W. J. Hardcastle and A. Marchal. Kluwer, pp. 241-261, Academic Publishers: The Netherlands. 1990

Wang, Y. and Kumaresan, R. (2006) Real Time Decomposition of Speech into Modulated Components. J Acoust Soc Am 119(6):EL68-EL73. 2006.

Zeng (2003). U.S. Pat. No. 7,225,027 (Regents of the University of California) Jun. 3, 2003

Zeng et al. (2005) Fan-Gang Zeng et al., Speech recognition with amplitude and frequency modulations, PNAS, vol. 102, no. 7, pp. 2293-2298, Feb. 15, 2005

Zhou, G., Hansen, J. H. L., and Kaiser, J. F. (2001) Nonlinear Feature Based Classification of Speech Under Stress. IEEE Transactions on Speech and Audio Processing 9(3):201-216. 2001.

The invention claimed is:

1. A signal processing device, comprising:
a signal processing unit configured to process an electrical SPU-input signal including frequencies in an audible frequency range between a minimum frequency and a maximum frequency, and configured to provide a processed SPU output signal, the signal processing unit including
an FM to AM transformation unit configured to transform an FM2AM input signal originating from the SPU-input signal and including at least a part of the frequency range of the SPU-input signal from a frequency modulated signal to an amplitude modulated signal, and configured to provide an FM2AM output signal, which is used in the generation of the processed SPU output signal, the FM to AM transformation unit including
a frequency demodulation unit configured to extract a frequency modulation function of the FM2AM input signal and configured to provide an FM2AM transformed signal, and
an AM modulator configured to perform amplitude modulation of the FM2AM input signal originating from the SPU-input signal with the FM2AM transformed signal to provide the FM2AM output signal.

2. A signal processing device according to claim 1 further comprising a time to time-frequency transformation unit providing a time varying representation of the SPU-input signal in a number of frequency ranges.

3. A signal processing device according to claim 1 comprising an AM-demodulation unit for extracting an amplitude modulation function $am_n(t)$ of the at least one signal originating from the SPU-input signal, n being a frequency range index.

4. A signal processing device according to claim 1 comprising a frequency demodulation unit for extracting a frequency modulation function $fm_n(t)$ of the at least one signal originating from the SPU-input signal, n being a frequency range index.

5. A signal processing device according to claim 4, wherein the FM to AM transformation of a signal originating from the SPU-input signal and comprising a frequency range p is based on the frequency modulation function $fm_n(t)$ extracted from a signal comprising a frequency range n, where p can be equal to n or different from n.

6. A signal processing device according to claim 4 comprising a carrier unit for providing a sinusoidal with a carrier frequency equivalent to the middle of a frequency range n and amplitude and an AM modulator for modulating the sinusoidal with the demodulated FM signal $fm_n(t)$ thereby providing the FM to AM transformation and the FM2AM output signal in frequency range n.

7. A signal processing device according to claim 4 comprising an AM modulator for modulating the SPU-input signal of the frequency range or channel n with the demodulated FM signal $fm_n(t)$, thereby providing the FM to AM transformation and the FM2AM output signal in frequency range n.

8. A signal processing device according to claim 4 comprising a combiner unit for combining the at least one signal originating from the SPU-input signal, the amplitude modulation function, the frequency modulation function and/or the FM2AM transformed signal with weights and providing a weighted amplitude modulation function.

9. A signal processing device according to claim 3 comprising a combiner unit for combining the extracted amplitude modulation function $am_n(t)$ and the FM2AM transformed signal of the corresponding frequency range with weights and providing a weighted amplitude modulation function.

10. A signal processing device according to claim 1 comprising a combiner unit for combining the at least one signal originating from the SPU-input signal and the FM2AM transformed signal with weights and providing a weighted amplitude modulation function.

11. A signal processing device according to claim 8, wherein
the combiner unit is configured to control the weights in dependence of the signal to noise ratio (SNR) of the SPU-input signal.

12. A signal processing device according to claim 8 comprising a carrier unit for providing a sinusoidal with a carrier frequency in, such as equivalent to the middle of, a frequency range n, and an AM modulator for amplitude modulating the sinusoidal with the weighted amplitude modulation function creating an amplitude modulated weighted output signal in that frequency range.

13. A signal processing device according to claim 8 comprising an AM modulator for amplitude modulating the SPU-input signal in a frequency range n with the weighted amplitude modulation function creating an amplitude modulated weighted output signal in that frequency range.

14. A signal processing device according to claim 1 comprising a FT-unit for providing a time-frequency to time transformation of a signal originating from the FM2AM signal(s) and/or from the weighted amplitude modulation functions and/or from the amplitude modulated weighted output signals to generate an SPU-output signal in the time domain.

15. A signal processing device according to claim 1, wherein
information contained in the frequency modulation of the electrical SPU-input signal is applied to the processed SPU output signal as amplitude modulation.

16. Use of a signal processing device according to claim 1 in a listening device, such as a hearing aid, e.g. a hearing instrument, or a head set, or a headphone or an active ear protection device.

17. A method of operating an audio processing device, the method comprising:
processing an SPU-input signal according to a user's needs, the SPU-input signal including frequencies in an audible frequency range between a minimum frequency and a maximum frequency; and
providing a processed SPU output signal, wherein
the processing the SPU-input signal according to a user's needs includes
providing an FM to AM transformation of an FM2AM input signal originating from the SPU-input signal and including at least a part of the frequency range of the SPU-input signal, and
providing an FM2AM output signal,
the providing the FM to AM transformation includes
extracting a frequency modulation function of the FM2AM input signal,
providing an FM2AM transformed signal based on said frequency modulation function, and
performing amplitude modulation of the FM2AM input signal originating from the SPU-input signal with the FM2AM transformed signal to provide said FM2AM output signal.

18. A method according to claim 17 wherein the processing of an SPU-input signal according to a user's needs comprises that the FM2AM signal is used to amplitude modulate a constant envelope input signal to provide a resulting amplitude modulated signal, which is used as a basis for the processed SPU output signal.

19. A data processing system comprising a processor and program code means for causing the processor to perform the steps of the method according to claim 17.

20. A non-transitory computer readable medium encoded with instructions, wherein the instructions, when executed on a processor, cause the processor to perform a method comprising:
processing an SPU-input signal according to a user's needs, the SPU-input signal including frequencies in an audible frequency range between a minimum frequency and a maximum frequency; and
providing a processed SPU output signal, wherein
the processing the SPU-input signal according to a user's needs includes
providing an FM to AM transformation of an FM2AM input signal originating from the SPU-input signal and including at least a part of the frequency range of the SPU-input signal, and
providing an FM2AM output signal,
the providing the FM to AM transformation includes
extracting a frequency modulation function of the FM2AM input signal,
providing an FM2AM transformed signal based on said frequency modulation function, and
performing amplitude modulation of the FM2AM input signal originating from the SPU-input signal with the FM2AM transformed signal to provide said FM2AM output signal.

* * * * *